United States Patent [19]

Cross et al.

[11] Patent Number: 4,551,468

[45] Date of Patent: Nov. 5, 1985

[54] HETEROCYCLIC THROMBOXANE SYNTHETASE INHIBITORS AND PHARMACEUTICAL COMPOSITIONS CONTAINING THEM

[75] Inventors: Peter E. Cross, Canterbury; Roger P. Dickinson, Dover; Geoffrey N. Thomas, Deal, all of England

[73] Assignee: Pfizer Inc., New York, N.Y.

[21] Appl. No.: 525,362

[22] Filed: Aug. 22, 1983

Related U.S. Application Data

[62] Division of Ser. No. 313,121, Oct. 20, 1981, Pat. No. 4,410,539.

[30] Foreign Application Priority Data

Oct. 23, 1980 [GB] United Kingdom ............... 8034198

[51] Int. Cl.[4] ..................... A61K 31/38; C07D 333/70
[52] U.S. Cl. .................................... 514/339; 514/337; 546/269; 546/272; 546/274
[58] Field of Search ....................... 546/269, 272, 274; 514/337, 339

[56] References Cited

FOREIGN PATENT DOCUMENTS 3560 8/1979 European Pat. Off. .

*Primary Examiner*—Henry R. Jiles
*Assistant Examiner*—Bernard I. Dentz
*Attorney, Agent, or Firm*—Charles J. Knuth; Albert E. Frost; Peter C. Richardson

[57] ABSTRACT

Heterocyclic thromboxane synthetase inhibitors of the formula

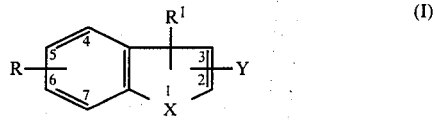

wherein $R^1$, which is attached to the 2-, 3- or 4-position, is hydrogen, halogen, $C_1$–$C_4$ alkyl, hydroxy or $C_1$–$C_4$ alkoxy;

Y, which is attached to the 2- or 3-position, is —COOH, —COO($C_1$–$C_4$ alkyl) or —CONH$_2$;

X is O, S, NH, N($C_1$–$C_4$ alkyl) or N(benzyl); and

R, which is attached to the 5-, 6- or 7-position, is a group of the formula

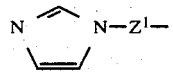

or (3- or 4-pyridyl)—$Z^2$— wherein $Z^1$ is —CH$_2$—, —CH$_2$CH$_2$— or —CH$_2$CH$_2$O— and $Z^2$ is —CH$_2$—, —CH$_2$CH$_2$—, —CH=CH—, —CH$_2$O— or —OCH$_2$—;

and their pharmaceutically acceptable salts; processes for their preparation, and pharmaceutical compositions containing them which are useful, for example, in the treatment of thrombosis.

10 Claims, No Drawings

HETEROCYCLIC THROMBOXANE SYNTHETASE INHIBITORS AND PHARMACEUTICAL COMPOSITIONS CONTAINING THEM

CROSS REFERENCE TO RELATED APPLICATION

This application is a division of application Ser. No. 313,121, filed Oct. 20, 1981 now U.S. Pat. No. 4,410,539.

BACKGROUND OF THE INVENTION

This invention relates to certain benzo-fused heterocycles, namely benzothiophenes, benzofurans and indoles, which are substituted by a carboxy, lower alkoxycarbonyl or carbamoyl group. Such compounds are able to selectively inhibit the action of the thromboxane synthetase enzyme without significantly inhibiting the action of the prostacyclin synthetase or cyclooxygenase enzymes. The compounds are thus useful as therapeutic agents, for example, in the treatment of thrombosis, ischaemic heart disease, stroke, transient ischaemic attack, migraine, cancer and the vascular complications of diabetes.

European Patent No. 3901, published Aug. 5, 1981, describes 3-(1-imidazol-1-ylalkyl)indoles in which the 2-position may be substituted with lower alkyl, lower cycloalkyl, adamantyl, phenyl or benzyl or substituted phenyl or benzyl groups. The compounds are reported as selective inhibitors of the thromboxane synthetase enzyme.

Other 3-(1-imidazol-1-ylalkyl)indoles useful as selective inhibitors of the thromboxane synthetase enzyme are reported in British Patent Application No. 2,045,244A, published Oct. 29, 1980. Said compounds may be substituted at the 2-position by alkyl, cycloalkyl phenyl or substituted phenyl, and are substituted at the 1-position by —X—Y wherein X is benzyl, furylmethyl, thienylmethyl or ($C_{1-3}$)alkylene; and Y is carboxy, carbalkoxy, carbamyl, cyano, 5-tetrazolyl, amino, acylamino, sulfamyl or substituted derivatives thereof.

European Patent Application No. 3560, published Aug. 22, 1979, describes 1-skatolylimidazole[3-(1-imidazolylmethyl)indole] and 1-(1-methylindole-2-ylmethyl)imidazole[1-methyl-2-(1-imidazolylmethyl)indole] as thromboxane synthetase inhibitors.

It has now been found that certain benzothiophenes, benzofurans and indoles in which the benzenoid ring is substituted by a 1-imidazolyl alkyl, a 2-(1-imidazolyl)ethoxy, a (3- or 4)-pyridylalkyl, pyridylvinyl, pyridyloxymethyl or pyridylmethoxy group are efficient inhibitors of the thromboxane synthetase inhibitor.

SUMMARY OF THE INVENTION

Thus according to the invention, there are provided compounds of the general formula

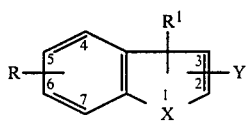

(I)

wherein $R^1$, which is attached to the 2-, 3- or 4-position, is hydrogen, halogen, $C_1$–$C_4$ alkyl, hydroxy or $C_1$–$C_4$ alkoxy;

Y, which is attached to the 2- or 3-position, is —COOH, —COO($C_1$–$C_4$ alkyl) or —CONH$_2$;

X is O, S, NH, N($C_1$–$C_4$ alkyl) or N(benzyl); and

R, which is attached to the 5-, 6- or 7-position, is a group of the formula

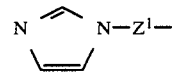

or (3- or 4-pyridyl)-$Z^2$-wherein $Z^1$ is —CH$_2$—, —CH$_2$CH$_2$— or —CH$_2$CH$_2$O— and $Z^2$ is —CH$_2$—, —CH$_2$CH$_2$—, —CH═CH—, —CH$_2$O— or —OCH$_2$—; and the pharmaceutically acceptable salts thereof.

"Halogen" means F, Cl, Br or I.

Alkyl and alkoxy groups of 3 or 4 carbon atoms may be straight or branched chain.

In the preferred compounds:

(a) X is S; Y is —COOH, —COOCH$_3$, —COOC$_2$H$_5$ or —CONH$_2$; $R^1$ is hydrogen, 3-chloro, 2- or 3-methyl, 4-methoxy or 4-hydroxy; and R is as defined for formula (I);

(b) X is O, R is (1-imidazolyl)methyl, (3-pyridyl)methyl, or (3-pyridyl)methoxy; $R^1$ is hydrogen or 3-methyl; and Y is —COOH, —COOCH$_3$ or —CONH$_2$; or (c) X is NH or N(benzyl); $R^1$ is hydrogen; R is (1-imidazolyl)methyl; and Y is —COOH or —COOCH$_3$.

A particularly preferred group are the compounds of section (a) above wherein Y is —COOH, $R^1$ is hydrogen, 2- or 3-methyl, or 4-methoxy, and R is (1-imidazolyl)methyl.

The particularly preferred individual compounds are those of the formula

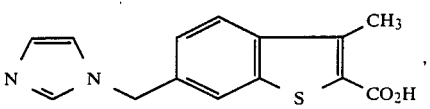

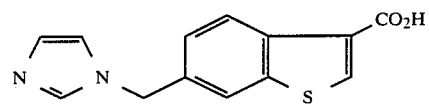

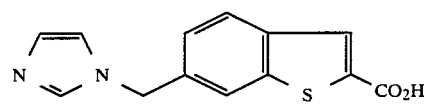

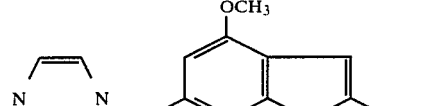

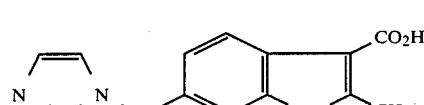

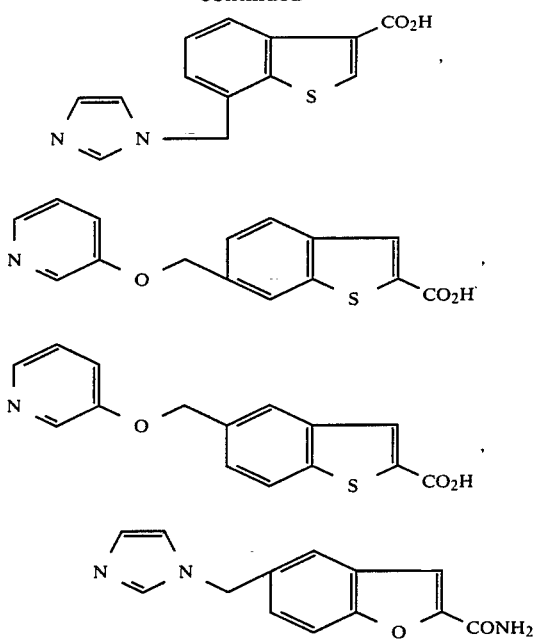

Another preferred group of compounds are those of formula I wherein X and Y are as previously defined; $R^1$, which is attached to the 2- or 3-position, is hydrogen, halogen, $C_1$-$C_4$ alkyl or $C_1$-$C_4$ alkoxy; and R, which is attached to the 5-, 6- or 7-position, is a group of the formula

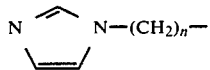

where n is 1 or 2;

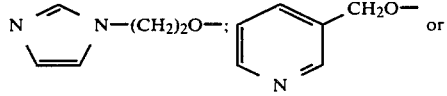

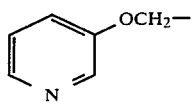

and the pharmaceutically acceptable acid addition salts thereof.

The invention also provides a method of inhibiting the action of the thromboxane synthetase enzyme in an animal, including a human being, without significantly inhibiting the action of the prostacyclin synthetase or cyclooxygenase enzymes, which comprises administering to the animal a thromboxane synthetase enzyme inhibiting amount of a compound of the formula (I), or a pharmaceutically acceptable salt thereof, or a pharmaceutical composition comprising a compound or salt together with a pharmaceutically acceptable diluent or carrier.

The invention further provides a compound of the formula (I), or a pharmaecutically acceptable salt thereof, for use in treating an animal, including a human being, to inhibit the action of the thromboxane synthetase enzyme without significantly inhibiting the action of the prostacyclin synthetase or cyclooxygenase enzymes.

The invention also includes a pharmaceutical composition comprising a compound of the formula (I), or a pharmaceutically acceptable salt thereof, together with a pharmaceutically acceptable diluent or carrier.

The preferred salts are the pharmaceutically acceptable acid addition salts, and, when Y is —COOH, the pharmaceutically acceptable metal or ammonium salts.

Pharmaceutically acceptable acid addition salts of the compounds of the invention are salts with acids containing pharmaceutically acceptable anions, e.g. the hydrochloride, hydrobromide, sulphate or bisulphate, phosphate or acid phosphate, acetate, maleate, fumarate, lactate, tartrate, citrate, gluconate, succinate and p-toluenesulphonate salts.

The preferred metal salts are the alkali metal salts.

DETAILED DESCRIPTION OF THE INVENTION

The compounds of the formula (I) can be prepared by a number of different routes, including the following:

(1) The imidazolyl-containing esters of the formula (I) in which X is O, S, N($C_1$-$C_4$ alkyl) or N(benzyl) and $R^1$ is other than hydroxy can be prepared as follows:

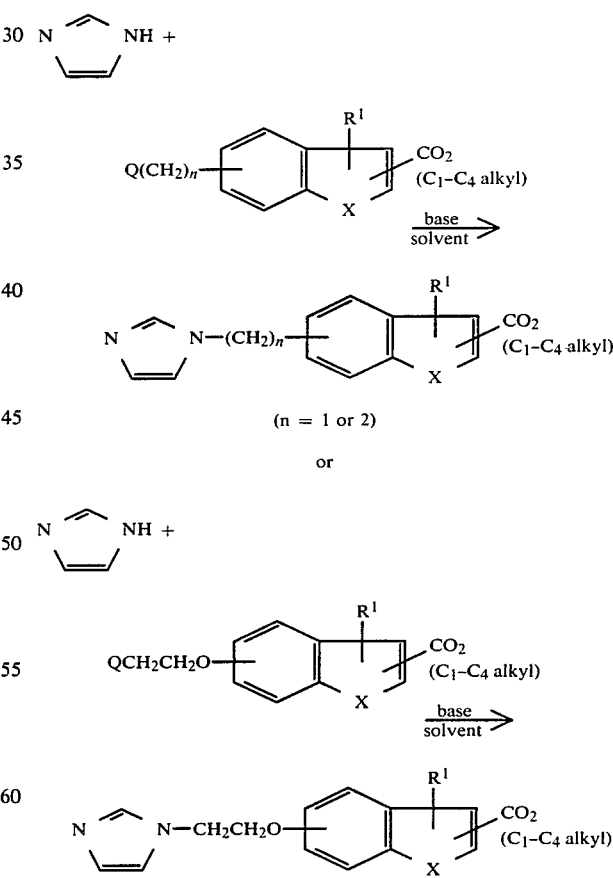

Q is a facile leaving group such as chloro, bromo, $C_1$-$C_4$ alkylsulphonyloxy or Ar $SO_2O$— where Ar is phenyl optionally substituted by 1 or 2 substituents selected from $C_1$-$C_4$ alkyl, $C_1$-$C_4$ alkoxy and halogen.

A preferred base is sodium hydride. Q is preferably Cl or Br.

Typical base/solvent combinations for the reaction are NaH/DMF, $C_2H_5ONa/C_2H_5OH$ and $Na_2CO_3$/acetone.

Typically the reaction proceeds to completion at room temperature, although in some cases heating, e.g. up to 100° C., is necessary to accelerate the reaction, which is generally complete in 8 hours or less. The product can be isolated and purified by conventional procedures.

(2) The imidazolyl-containing esters of the formula (I) in which X is O, S, N($C_1$-$C_4$ alkyl) or N(benzyl) and $R^1$ is other than hydroxy can be prepared as follows:

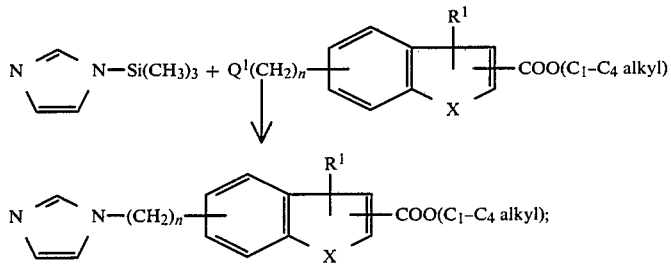

(n = 1 or 2)

or

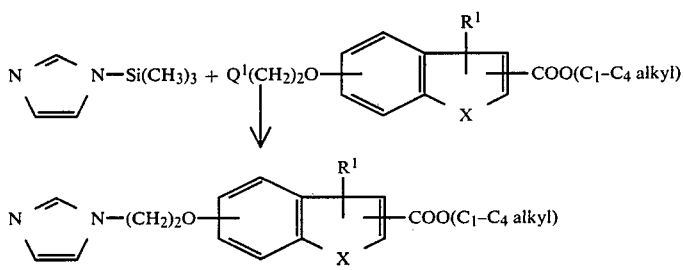

($Q^1$ = Cl or Br)

Typically the reaction is carried out in an organic solvent, e.g. toluene, by heating at up to 110° C. for up to 4 hours. The product can be isolated and purified by conventional procedures.

Esters in which X is NH can be prepared via this route by using an indole starting material in which X is N-acetyl. The acetyl group is removed after reaction by mild base treatment, e.g. using ethanolic ammonia/room temperature.

(3) The pyridyloxymethyl ester in which $R^1$ is other than hydroxy can be prepared as follows:

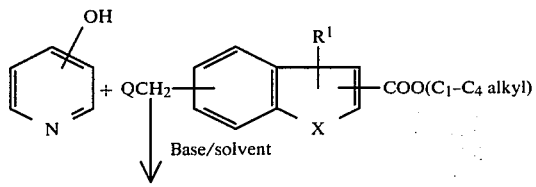

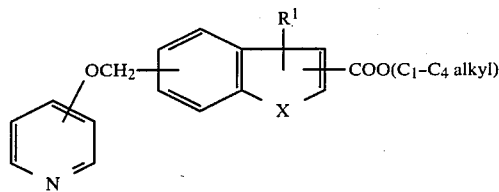

Q is as defined in Route (1).

The preferred base/solvent combination is NaH/dimethylformamide. Typically the reaction proceeds to completion at room temperature in 6 hours or less, but heating at up to 100° C. may in some cases be necessary, and again the product can be isolated and purified by conventional procedures.

(4) The puridylmethoxy esters in which $R^1$ is other than hydroxy can be prepared as follows:

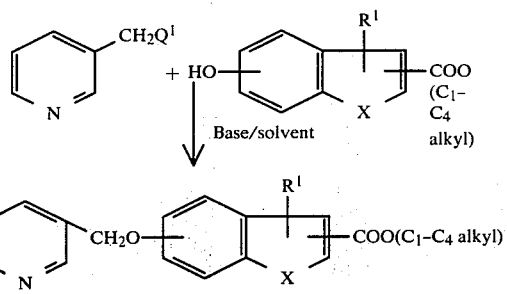

$Q^1$ is Cl or Br.

The reaction can be carried out similarly to Route (3). The preferred base/solvent combinations are NaH/DMF and EtONa/EtOH. Often the pyridine starting materials are available as hydrochlorides, which can be converted to the free base in situ by using an extra equivalent of base.

(5) The pyridyl vinyl esters of the formula (I) can be prepared by the Wittig reaction as follows:

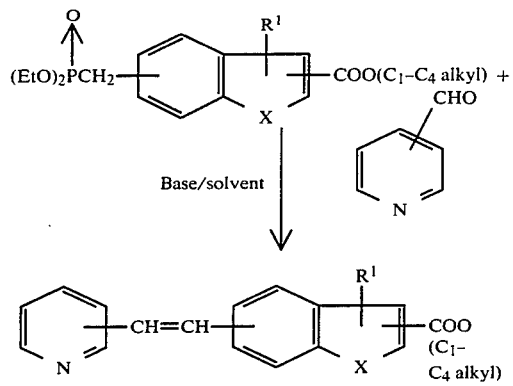

The reaction can generally be carried out by stirring the reaction mixture at room temperature for a few hours, although in some cases heating at up to 100° C. may be necessary, the preferred base/solvent combination being sodium hydride/dimethoxyethane, and again the product can be isolated and purified by conventional procedures. The reaction is generally complete in 24 hours or less.

If desired, the vinyl esters can be converted to their pyridylethyl analogues by hydrogenation over e.g. Pt/C or Pd/C. The phosphorus-containing starting materials are available by the method in Example 23 using triethyl phosphite.

(6) The vinyl esters can also be prepared by the Heck reaction (Acc. Chem. Res. 12, 146, 1979):

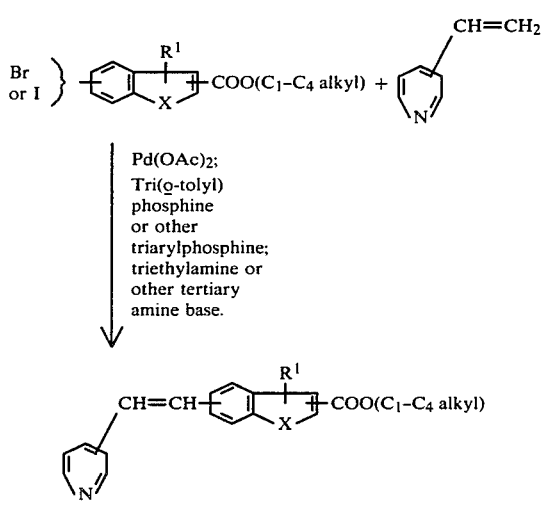

The reaction is typically carried out by heating the reactants at 70°–130° C. under an atmosphere of nitrogen for up to about 24 hours. The product can be isolated and purified by conventional procedures.

(7) The 2-carboxy compounds of the formula (I) can be prepared as follows:

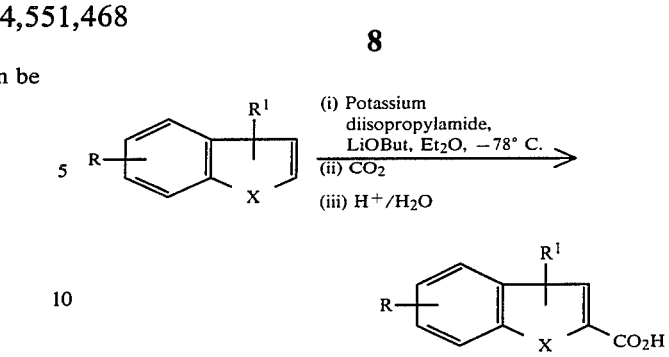

In a typical procedure, n-butyl lithium as a solution in hexane is added dropwise to a stirred mixture of diisopropylamine and potassium t-butoxide in dry ether at −78° C. under dry nitrogen. After stirring for about an hour at this temperature the benzo-fused heterocycle is added in e.g. dry ether, and the reaction mixture is again stirred at this temperature for about an hour. Excess crushed solid $CO_2$ is then added, and, after all the $CO_2$ has evaporated, water is added and the mixture shaken. The aqueous layer is separated, washed with ether, acidified with e.g. acetic acid, and the solid filtered off and dissolved in sodium hydroxide. The solution can be decolorized by warming with charcoal, filtered, acidified with e.g. acetic acid, and the resulting solid filtered off, washed with water, and dried to give the desired product.

(8) The 2- and 3-carboxy compounds can also be prepared as follows:

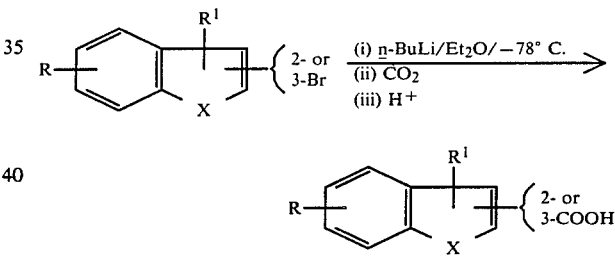

In a typical procedure, n-butyl lithium as a solution in hexane is added to the benzo-fused heterocycle in e.g. dry ether at −78° C. under dry nitrogen. After stirring at −78° C. for a short time, an excess of crushed solid $CO_2$ is added. The remaining steps can then be carried out similarly to procedure (7) above.

(9) Cyclization can also be used to prepare certain of the benzofurans of the formula (I):

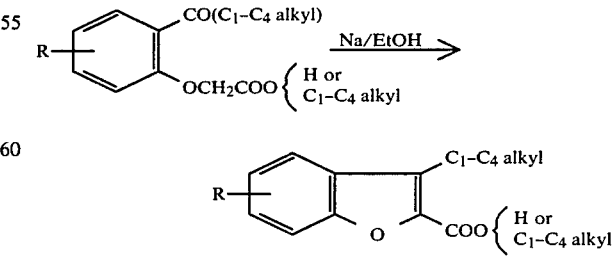

The reaction can be carried out by refluxing the reactants together for up to about 4 hours. The product can then be isolated by conventional procedures.

(10) Some of the compounds of the invention can be prepared from other compounds of the invention, e.g. the acids can be prepared by the acidic (e.g. HCl) or basic (e.g. KOH) hydrolysis of the corresponding esters. Similarly reaction of the esters with ammonia produce the amides, which can also be prepared by reaction of the corresponding acids with carbonyl diimidazole and then with ammonia. Compounds in which $R^1$ is hydroxy can be obtained by the reaction of the corresponding methoxy compound with aqueous hydrobromic acid (when the substrate is sufficiently stable) or with boron tribromide. The N-benzyl indoles can be prepared from the corresponding N-H derivatives using sodium hydride and benzyl bromide.

Pharmaceutically acceptable salts can be prepared by conventional procedures, e.g. by reacting an organic solution of the compound with an organic solution of a suitable acid to obtain an acid addition salt either by precipitation, or by evaporation of the solution.

The starting materials used in the previous routes are either known compounds or can be prepared by procedures analogous to those of the prior art. The preparation of novel starting materials used in the Examples is in fact illustrated in detail hereinafter and these methods will in general be application to the preparation of analogous compounds as will be known to those skilled in the art.

The compounds of formula (I) and their pharmaceutically acceptable salts have been found to selectively inhibit the action of the thromboxane synthetase enzyme without significantly affecting the action of the prostacyclin synthetase or cyclooxygenase enzymes. Thus the compounds are of value in the treatment of a variety of clinical conditions which are characterized by an imbalance of prostacycline/thromboxane $A_2$. For the reasons given below these conditions include thrombosis, ischaemic heart disease, stroke, transient ischaemic attack, migraine, cancer and the vascular complications of diabetes.

Research work has established that in most tissues the major product of the arachidonic acid metabolism is either of two unstable substances, thromboxane $A_2$ ($TxA_2$) or prostacyclin ($PGI_2$). (Proc. Nat. Acad. Sci. U.S.A., 1975, 72, 2994; Nature 1976, 263, 663; Prostaglandins, 1976, 12, 897). In most cases the prostaglandins $PGE_2$, $PGF_2$ and $PGD_2$ are comparatively minor by-products in this biosynthetic pathway. The discovery of thromboxane $A_2$ and prostacyclin has significantly increased our understanding of vascular homeostasis. Prostacyclin for instance is a powerful vasodilator and inhibitor of platelet aggregation, and in this last respect is the most potent endogenous substance so far discovered. The prostacyclin synthethase enzyme is located in the endothelial layer of the vasculature, and may be fed by endoperoxides released by blood platelets coming into contact with the vessel wall. The prostacyclin thus produced is important for prevention of platelet deposition on vessel walls. (Prostaglandins, 1976, 12, 685; Science, 1976, 17; Nature, 1978, 273, 765).

Thromboxane $A_2$ is synthesized by the thromboxane synthetaste enzyme which is located in, for example, the blood platelets. Thromboxane $A_2$ is a powerful vasoconstrictor and pro-aggegatory substance. As such its actions are in direct opposition to those of prostacyclin. If, for any reason, prostacyclin formation by the vasculature is impaired, then the endoperoxides produced by platelets coming into contact with the vessel wall are converted to thromboxane, but are not converted effectively into prostacyclin (Lancet, 1977, 18; Prostaglandins, 1978, 13, 3). Alteration of the prostacyclin/thromboxane balance in favor of the latter substance could result in platelet aggregation, vasospasm (Lancet, 1977, 479; Science, 1976, 1135, Amer. J. Cardiology, 1978, 41, 787) and an increased susceptibility to atherothrombosis (Lancet (i) 1977, 1216). It is also known that in experimental atherosclerosis prostacyclin generation is suppressed and thromboxane $A_2$ production is enhanced (Prostaglandins, 1977, 14, 1025 and 1035). Thus thromboxane $A_2$ has been implicated as the causative agent in various angina, myocardial infarction, sudden cardiac death and stroke (Thromb. Haemostasis, 1977, 38, 132). Studies in rabbits have shown that ECG changes typical of these conditions were produced when freshly prepared thromboxane $A_2$ was injected directly into the animal's heart (Biochem. Aspects of Prostaglandins and Thromboxanes, Editors, N. Kharasch and J. Fried, Academic Press, 1977, page 189). This technique is considered to represent a unique animal model of the heart attacks of coronary patients and has been used to show that administration of a compound believed to antagonize the effects of thromboxane $A_2$ protects the rabbits from the adverse consequences of thromboxane $A_2$ injection.

Another area where a $PGI_2/TxA_2$ imbalance is considered to be a contributory factor is that of migraine.

The migraine headache is associated with changes in intra and extracerebral blood flow, in particular a preheadache reduction of cerebral blood flow followed by dilatation in both vascular areas during the headache phase.

Prior to the development of the headache, blood levels of 5-hydroxytryptamine are elevated, and this suggests the occurrence of in vivo aggregation and release of the amine from the platelet stores. It is known that the blood platelets of migraine patients are more prone to aggregate than are those of normal individuals (J. Clin. Pathol., 1971, 24, 250; J. Headache, 1977, 17, 101). Furthermore, it has now been postulated that not only is an abnormality of platelet function a major factor in the pathogenesis of migraine attacks but it is in fact their prime cause (Lancet (i), 1978, 501). Thus a drug that selectively modifies platelet function to inhibit thromobxane $A_2$ formation could be of considerable benefit in migraine therapy.

Abnormalities of platelet behavior have been reported in patients with diabetes mellitus (Metabolism, 1979, 28, 394; Lancet, 1978 (i), 235). Diabetic patients are known to be particularly susceptible to microvascular complications, atherosclerosis and thrombosis and platelet hyper-reactivity has been suggested as the cause of such angiopathy. Diabetic platelets produce elevated amounts of $TxB_2$ and malodialdehyde (Symposium "Diabetes and Thrombosis-Implications for Therapy", Leads U.K., April 1979). Also it has been shown that in rats with experimental diabetes vascular prostacyclin production is impaired and $TxA_2$ synthesis from the platelets is elevated (IV International Prostaglandin Conference, Washington, D.C., May 1979). Thus the imbalance between prostacyclin and $TxA_2$ is considered to be responsible for the microvascular complications of diabetes. A $TxA_2$-synthetase inhibitor could therefore find clinical utility in preventing these vascular complications.

Aspirin and most other non-steroidal antiinflammatory drugs inhibit the cyclooxygenase enzyme. The effect of this is to shut down the production of PGG$_2$/H$_2$ endoperoxides and by so doing to reduce the prostacyclin and thromboxane A$_2$ levels. Aspirin and aspirin-like drugs have been evaluated clinically for prevention of stroke and heart attack (New England and J. Med. 1978, 299, 53; B.M.J., 1978, 1188; Stroke, 1977, 8, 301).

Although some encouraging results have been obtained with these drugs, a compound which specifically inhibits thromboxane A$_2$ formation leaving the biosynthesis of prostacyclin unimpaired would be more valuable in these clinical conditions (Lancet (ii), 1978, 780).

The ability of primary neoplasms to metastasize is a principal cause of failure to cure human cancers. It has been suggested that metastatic tumor cells can alter the critical PGI$_2$-TxA$_2$ balance in favor of thrombosis (Science, 1981, 212, 1270). Prostacyclin has recently been shown to be a powerful antimetastatic agent by virtue of its platelet antiaggregatory action. This result indicates that a TxA$_2$-synthetase inhibitor would function as an antimetastatic agent in vivo (J. Cell. Biol. 1980, 87, 64).

The effect of the compounds of the formula (I) on the thromboxane synthetase enzyme, and the prostacyclin synthetase and cyclooxygenase enzymes has been measured by the following in vitro enzyme assays:

1. Cyclooxygenase

Ram seminal vesicle microsomes (Biochemistry, 1971, 10, 2372) are incubated with arachidonic acid (100 μM:1 min.:22° C.) to produce PGH$_2$ and aliquots of the reaction mixture injected into a stream of Krebsbicarbonate at 37° C. (containing a mixture of antagonists (Nature, 1978, 218, 1135) and indomethacin (Brit. J. Pharmacol., 1972, 45, 451) which is superfusing a spirally-cut rabbit aorta strip (Nature, 1969, 223, 29).

The ability of a compound to inhibit the enzyme is measured by comparing the increases in isometric tension produced by PGH$_2$ in the absence of the test compound, and following pre-incubation of the enzyme with the test compound for 5 minutes (Agents and Actions, 1981, 11, 274).

2. Prostacyclin (PGI$_2$) Synthetase

Pig aorta microsomes (Nature, 1976, 263, 663) are incubated (30 sec.; 22° C.) with PGH$_2$ produced as in 1 and the reaction terminated with 5 volumes of ethanol. PGI$_2$ production is assessed by measuring its stable breakdown product, 6-keto PGF$_2$α, using a specific radioimmunoassay. PGI$_2$ production can be completely inhibited by pre-incubation of the enzyme with the selective PGI$_2$ synthetase inhibitor, 15-hydroperoxyarachidonic acid (Prostaglandins, 1976, 12, 715). The test compound is pre-incubated with the enzyme for 5 minutes, and its ability to prevent the production of PGI$_2$ (6-keto PGF$_1$α) is measured.

3. Thromboxane A$_2$ (TxA$_2$) Synthetase

Indomethacin pretreated human platelet microsomes (Science 1976, 193, 163) are incubated (2 min.:0° C.) with PGH$_2$ (produced as in 1) and the reaction terminated with 5 volumes of ethanol. TxA$_2$ production is assessed by measuring its stable metabolite TxB$_2$, using a specific radioimmunoassay.

The test compound is pre-incubated with enzyme for 5 minutes, and its ability to inhibit the thromboxane synthetase enzyme is measured as reduction of the TxA$_2$ (TxB$_2$) production.

Compounds of the formula (I) tested in this way have been shown to be capable of selectively inhibiting the thromboxane synthetase enzyme.

In addition to the above an in vitro assay for measuring the inhibition of human blood platelet aggregation has been described and this may be predictive of antithrombotic efficacy clinically (Lancet (ii), 1974, 1223; J. Exp. Med., 1967, 126, 171). Both clinically effective agents aspirin and sulphinpyrazone show inhibitory activity in vitro against a variety of aggregating agents in this test.

A number of in vitro tests in animals have also been described for evaluating potential antithrombotic drugs.

The method of Patrono et al., (Thrombosis Research, 17, 317–327 [1980]) was adapted to study the generation of TxB$_2$ in whole blood samples removed from animals prior to and following drug treatment. Briefly, blood samples are taken into glass tubes and allowed to clot at 37° C. Serum is separated by centrifugation and the samples stored at −40° C. until assayed for TxB$_2$, when appropriate dilutions of ethanol deproteinized samples were analyzed by RIA. This technique is used in experiments with the test compounds to determine intravenous potency in anesthetized rabbits:

Anesthetized Rabbits

Male New Zealand white rabbits (2.6–5.6 kg.) are anesthetized with sodium pentobarbitone (30 mg./kg. i.v.) followed by urethane (500 mg./kg. i.p.). After cannulation of the trachea, a carotid artery is catheterized for collection of blood samples. The catheter is kept patent by slow infusion (0.2 mg./min.) of sterile saline. Control carotid arterial blood samples were taken 30 and 5 minutes prior to administration of the test compound or vehicle (0.9% w/v NaCl, 0.2 ml./kg.) via a marginal ear vein. Three groups of rabbits are used. The first group receive 0.03 mg./kg. of the test compound followed, one hour later, by 0.1 mg./kg. Similarly, the second group receive 0.3 mg./kg., followed by 1 mg./kg. The third group receive vehicle, followed one hour later by a further vehicle injection. Carotid arterial blood samples are taken 15 and 45 minutes after all doses. At each time point, a 1 ml. blood sample is taken into a glass test tube, without anticoagulant, for TxB$_2$ determination. For the latter, the blood sample is allowed to clot during a two hour incubation at 37° C. (which preliminary experiments had shown to give maximum TxB$_2$ production) and the serum obtained by centrifugation. Serum samples are then processed through the TxB$_2$ RIA after deproteinization with ethanol and dilution with Isogel Tris buffer.

Intravenous injection of arachidonic acid causes death in rabbits by causing platelet clumping and embolization in the lungs. Again both the clinically effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platelets in an extra corporeal loop of the abdominal aorta of rats in vivo (Thromb. Diathes. Haem., 1973, 30, 138).

The compounds can be administered orally in the form of tablets or capsules containing a unit dose of the compound together with such excipients as maize starch, calcium carbonate, dicalcium phosphate, alginic acid, lactose, magnesium stearate, "Primogel" (Trademark) or talc. The tablets are typically prepared by granulating the ingredients together and compressing the resulting mixture to give tablets of the desired size. Capsules are typically prepared by granulating the ingredients together and filling them into hard gelatin capsules of the appropriate size to contain the desired dosage.

The compounds can also be administered parenterally, for example by intramuscular, intravenous or subcutaneous injection. For parenteral administration, they are best used in the form of a sterile aqueous solution which may contain other solutes such as tonic and pH adjusters. The compounds may be added to distilled water and the pH adjusted to 3–6 using an acid such as citric, lactic or hydrochloric acid. Sufficient solutes such as dextrose or saline may be added to render the solution isotonic. The resulting solution may then be sterilized and filled into sterile glass vials of an appropriate size to contain the desired volume of solution. The compounds of the invention may also be administered by the infusion of a parenteral formulation as described above into a vein.

For oral administration to human patients, it is expected that the daily dosage level of a compound of the formula (I) will be from 0.1 to 20 mg./kg. per day for a typical adult patient (70 kg.). For parenteral administration, it is expected that the daily dosage level of a compound of the formula (I) will be from 0.01–0.5 mg./kg. per day, for a typical adult patient. Thus tablets or capsules can generally be expected to contain from 5 to 150 mg. of the active compound for administration orally up to 3 times a day. Dosage units for parenteral administration can be expected to contain from 0.5–35 mg. of the active compound. A typical vial could be a 10 ml. vial containing 5 mg. of the active compound in 6–10 ml. of solution.

It should of course be appreciated that in any event the physician will determine the actual dosage which will be most suitable for the individual and it will vary with the age, weight and response of the patient.

The above dosages are exemplary of the average patient, there may of course be individual cases where higher or lower dosage ranges are merited.

The preparation of the novel compounds of the formula (I) is illustrated by the following Examples. All temperatures are in °C.

EXAMPLE 1

5-(1-Imidazolylmethyl)benzo[b]thiophene-2-Carboxylic Acid Methyl Ester (i) 5-Methylbenzo[b]thiophene-2-carboxylic acid methyl ester Hydrogen chloride gas was passed into a solution of 5-methylbenzo[b]thiophene-2-carboxylic acid (7.50 g.) in methanol (250 ml.) until the solution was saturated. The solution was heated under reflux for 1 hour and then evaporated. The residue was washed with water and crystallized from methanol to give 5-methylbenzo[b]thiophene-2-carboxylic acid methyl ester (7.80 g.) m.p. 78°–79°.

Analysis: Found: C, 63.69; H, 4.80. $C_{11}H_{10}O_2S$ requires: C, 64.05; H, 4.89%.

(ii) 5-Bromomethylbenzo[b]thiophene-2-carboxylic acid methyl ester

A mixture of 5-methylbenzo[b]thiophene-2-carboxylic acid methyl ester (3.09 g.), N-bromosuccinimide (2.67 g.) and azobisisobutyronitrile (0.20 g.) in carbon tetrachloride (150 ml.) was heated under reflux for 5 hours. The mixture was then filtered and the filtrate was evaporated to give a solid which was crystallized from methanol to give 5-bromomethylbenzo[b]thiophene-2-carboxylic acid methyl ester (4.16 g.), m.p. 108°–110°.

(iii) 5-(1-Imidazolylmethyl)benzo[b]thiophene-2-carboxylic acid methyl ester

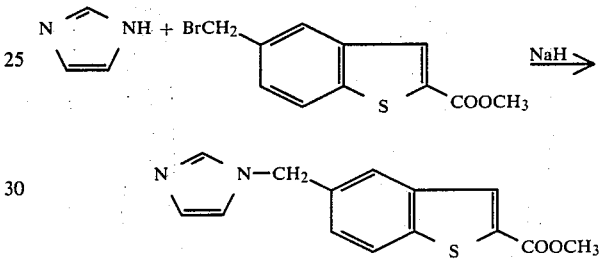

NaH (0.34 g.:50% dispersion in oil) was added portionwise to a stirred solution of imidazole (0.48 g.) in dry dimethylformamide (DMF) (20 ml.). After ½ hour a solution of 5-bromomethylbenzo[b]thiophene-2-carboxylic acid methyl ester (2.0 g.) in DMF (15 ml.) was added dropwise. After stirring at room temperature for 1 hour, the solvent was removed under reduced pressure and $H_2O$ (100 ml.) added to the residue. The aqueous solution was then extracted with EtOAc ($3 \times 50$ ml.) and the combined organic extracts were washed ($H_2O$), dried ($MgSO_4$), filtered and evaporated to give a solid which was recrystallized from $MeOH/H_2O$ to give 5-(1-imidazolylmethyl)benzo[b]thiophene-2-carboxylic acid methyl ester, 0.7 g., m.p. 168°–169° C.

Analysis: Found: C, 61.60; H, 4.40; N, 9.95. $C_{14}H_{12}N_2O_2S$ requires: C, 61.74; H, 4.44; N, 10.29%.

EXAMPLES 2–6

Other novel benzo[b]thiophenecarboxylic acid esters prepared by the method of Example 1(i) are listed in Table 1.

TABLE 1

| Structure | m.p. °C. | Recrystn. Solvent | Analysis | |
|---|---|---|---|---|
| ![CH3-benzothiophene-CO2CH3] | 92–95.5° | Methanol | Found: C, 64.04; H, 4.84. Requires: C, 64.05; H, 4.89%. | $C_{14}H_{12}N_2O_2S$ |

TABLE 1-continued

| Structure | m.p. °C. | Recrystn. Solvent | Analysis |
|---|---|---|---|
| CH₃–[benzothiophene]–CO₂CH₃ | b.p. 110° @ 0.1 m.m. | — | Used directly |

Other bromomethylbenzo[b]thiophenecarboxylic acid esters prepared by the method of Example 1(ii) are listed in Table 2.

Other (1-imidazolylmethyl)benzo[b]thiophenecarboxylic acid esters of the invention prepared by the method of Example 1(iii) are listed in Table 3.

TABLE 2

| Structure | m.p. °C | Recrystn. | Analysis | | |
|---|---|---|---|---|---|
| BrCH₂–[benzothiophene]–CO₂CH₃ (5-BrCH₂, 2-CO₂CH₃) | 102.5–106 | Methanol/H₂O | Found: | C, 46.75; H, 3.20. | $C_{11}H_9BrO_2S$ |
| | | | Requires: | C, 46.32; H, 3.18%. | |
| [benzothiophene with CH₂Br at 7, CO₂CH₃ at 2] | 95–98 | Ethyl acetate/petrol (b.p. 60–80) | Found: | C, 45.83; H, 3.14. | $C_{11}H_9BrO_2S$ |
| | | | Requires: | C, 46.32; H, 3.18%. | |
| BrCH₂–[benzothiophene-Cl]–CO₂CH₃ | 152–154 | Chloroform/Petrol (b.p. 60–80) | Found: | C, 41.03; H, 2.54. | $C_{11}H_8BrClO_2S$ |
| | | | Requires: | C, 41.33; H, 2.52%. | |
| BrCH₂–[benzothiophene]–CO₂CH₃ (3-CO₂CH₃) | 133–135 | Ether | Found: | C, 46.60; H, 3.05. | $C_{11}H_9BrO_2S$ |
| | | | Requires: | C, 46.32; H, 3.18%. | |
| [benzothiophene with CO₂CH₃ at 3, CH₂Br at 7] | 90 | Ether/petrol (b.p. 40–60) | Found: | C, 46.54; H, 3.16. | $C_{11}H_9BrO_2S$ |
| | | | Requires: | C, 46.32; H, 3.18%. | |

TABLE 3

| Example | Structure | m.p. °C. | Recrystn. Solvent | Analysis |
|---|---|---|---|---|
| 2 | imidazolyl-CH₂–[benzothiophene]–CO₂CH₃ | 143–144 | Isopropanol | Found: C, 61.40; H, 4.50; N, 10.20. $C_{14}H_{12}N_2O_2S$ Requires: C, 61.74; H, 4.44; N, 10.29%. |
| 3 | [benzothiophene with CO₂CH₃ at 2, CH₂-imidazolyl at 7] | 125–126 | Ethyl acetate/petrol (b.p. 60–80) | Found: C, 61.45; H, 4.42; N, 9.93. $C_{14}H_{12}N_2O_2S$ Requires: C, 61.74; H, 4.44; N, 10.29%. |
| 4 | imidazolyl-CH₂–[benzothiophene-Cl]–CO₂CH₃ | 170–172 | chloroform/petrol (b.p. 60–80) | Found: C, 54.64; H, 3.56; N, 9.31. $C_{14}H_{11}ClN_2O_2S$ Requires: C, 54.81; H, 3.61; N, 9.13%. |

TABLE 3-continued

| Example | Structure | m.p. °C. | Recrystn. Solvent | Analysis |
|---|---|---|---|---|
| 5 | (imidazolylmethyl-benzo[b]thiophene-CO₂CH₃) | 212–214* | isopropanol | Found: C, 54.25; H, 4.25; N, 9.40. C$_{14}$H$_{12}$N$_2$O$_2$S.HCl Requires: C, 54.45; H, 4.24; N, 9.10%. |
| 6 | (benzo[b]thiophene-CO₂CH₃ with imidazolylmethyl at 7-position) | 136–138 | Ethyl acetate/ petrol (b.p. 60–80) | Found: C, 61.48; H, 4.55; N, 10.29. C$_{14}$H$_{12}$N$_2$O$_2$S Requires: C, 61.74; H, 4.44; N, 10.29%. |

EXAMPLE 7

6-(1-Imidazolylmethyl)benzo[b]thiophene-3-carboxylic acid methyl ester (i) 2,3-Dibromo-6-methylbenzo[b]thiophene Bromine (15.2 g.) was added dropwise over 5 minutes to a stirred solution of 6-methylbenzo[b]thiophene (7.0 g.) in chloroform (70 ml.) at room temperature. The resulting solution was stirred at room temperature for 4 hours and then evaporated. The residue was crystallized from methanol to give 2,3-dibromo-6-methylbenzo[b]thiophene (12.4 g.), m.p. 67.5°–68.5° C.

Analysis %: Found: C, 35.09; H, 1.90. C$_9$H$_9$Br$_2$S Requires: C, 35.33; H, 1.98%.

(ii) 3-Bromo-6-methylbenzo[b]thiophene

A solution of n-butyl lithium (22.3 ml. of 1.6M solution in hexane) was added dropwise to a stirred solution of 2,3-dibromo-6-methylbenzo[b]thiophene (11.76 g.) in dry ether (150 ml.) at 0° under an atmosphere of dry nitrogen. The resulting solution was stirred at 0° for 1 hour and then water (50 ml.) was added. The mixture was stirred for a few minutes and then the ether layer was separated, dried (Na$_2$SO$_4$) and evaporated to give an oil. The oil was distilled to give 3-bromo-6-methylbenzo[b]thiophene (5.80 g.), b.p. 112°–114° C. @ 0.2 m.m., m.p. 51°–53° C. (from methanol).

(iii) 6-Methylbenzo[b]thiophene-3-carboxylic acid

A solution of n-butyl lithium (15 ml. of 1.0M solution in hexane) was added dropwise to a stirred solution of 3-bromo-6-methylbenzo[b]thiophene (3.0 g.) in dry ether (40 ml.) at −70° C. under an atmosphere of dry nitrogen. The mixture was stirred at −70° C. for 30 minutes and then an excess of crushed solid carbon dioxide was added. When all the carbon dioxide had evaporated, water (25 ml.) was added and the mixture was stirred for a few minutes. The organic layer was separated and washed with 2N.NaOH solution. The aqueous layer and NaOH extract were combined and acidified with concentrated hydrochloric acid. The solid was filtered off, washed with water, dried and crystallized from toluene to give 6-methylbenzo[b]thiophene-3-carboxylic acid (1.60 g.), m.p. 205°–209°.

Analysis: Found: C, 62.31; H, 4.17. C$_{10}$H$_8$O$_2$S Requires: C, 62.48; H, 4.20%.

(iv) 6-Methylbenzo[b]thiophene-3-carboxylic acid methyl ester

Treatment of the above acid with methanol in the presence of hydrogen chloride by the method of Example 1(i) gave 6-methylbenzo[b]thiophene-3-carboxylic acid methyl ester, m.p. 82°–84° (from petrol b.p. 40°–60°).

Analysis: Found: C, 63.92; H, 4.86. C$_{11}$H$_{10}$O$_2$S Requires: C, 64.05; H, 4.89%.

(v) 6-Bromomethylbenzo[b]thiophene-3-carboxylic acid methyl ester

Treatment of the above ester with N-bromosuccimimide and azobisisobutyronitrile by the method of Example 1(ii) gave 6-bromomethylbenzo[b]thiophene-3-carboxylic acid methyl ester, m.p. 165°–167° (from ethyl acetate/petrol b.p. 60°–80°).

Analysis: Found: C, 46.05; H, 3.13. C$_{11}$H$_9$BrO$_2$S Requires: C, 46.33; H, 3.18%.

(vi) 6-(1-Imidazolylmethyl)benzo[b]thiophene-3-carboxylic acid methyl ester

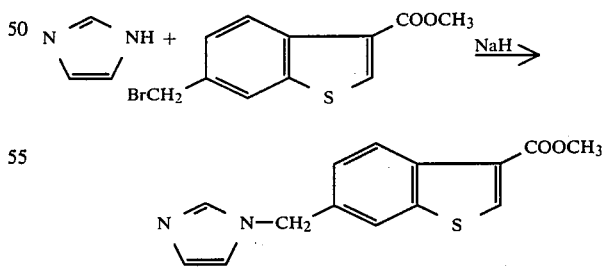

Successive treatment of imidazole with sodium hydride and 6-bromomethylbenzo[b]thiophene-3-carboxylic acid methyl ester according to the method of Example 1(iii) gave 6-(1-imidazolylmethyl)benzo[b]thiophene-3-carboxylic acid methyl ester, m.p. 117°–118.5° C. (from ethyl acetate/petrol b.p. 60°–80°).

Analysis: Found: C, 61.53; H, 4.47; N, 10.29. C$_{14}$H$_{12}$N$_2$O$_2$S Requires: C, 61.74; H, 4.44; N, 10.29%.

EXAMPLE 8

5-(1-Imidazolylmethyl)-3-methylbenzo[b]thiophene-2-carboxylic acid methyl ester

(i) 5-Hydroxymethyl-3-methylbenzo[b]thiophene

A solution of 3-methylbenzo[b]thiophene-5-carboxylic acid ethyl ester (14.44 g.) in dry ether (50 ml.) was added dropwise with stirring to a mixture of lithium aluminium hydride (5.32 g.) in dry ether (450 ml.) under an atmosphere of dry nitrogen. Sufficient heat was applied during the addition to maintain gentle reflux. The mixture was heated under reflux with stirring for 3 hours and then cooled. The excess of lithium aluminium hydride was decomposed by the cautious addition with stirring of water (5.3 ml.) followed by 5N sodium hydroxide solution (5.3 ml.) and finally more water (16 ml.). The mixture was filtered and the filtrate was dried ($Na_2SO_4$) and evaporated to give an oil which crystallized on standing. The solid was crystallized from ether/petrol (b.p. 40°–60°) to give 5-hydroxymethyl-3-methylbenzo[b]thiophene (8.93 g.), m.p. 51°–53°.

Analysis: Found: C, 67.32; H, 5.66. $C_{10}H_{10}OS$ Requires: C, 67.38; H, 5.73%.

(ii) 5-Hydroxymethyl-3-methylbenzo[b]thiophene-2-carboxylic acid

A solution of 5-hydroxymethyl-3-methylbenzo[b]thiophene (8.50 g.) in dry ether (120 ml.) was added dropwise to a stirred solution of n-butyl lithium (72 ml. of 1.6M solution in hexane) in dry ether (120 ml.) at 0° under an atmosphere of dry nitrogen. The resulting mixture was stirred at 0° for 2 hours and then poured onto a mixture of crushed solid carbon dioxide and ether. When all the carbon dioxide had evaporated the mixture was shaken with water. The aqueous layer was separated and acidified with concentrated hydrochloric acid. The solid was filtered off, washed well with water and crystallized from ethanol to give 5-hydroxymethyl-3-methylbenzo[b]thiophene-2-carboxylic acid (4.80 g.), m.p. 260°–262°.

Analysis: Found: C, 59.52; H, 4.70. $C_{11}H_{10}O_3S$ Requires: C, 59.44; H, 4.54%.

(iii) 5-Chloromethyl-3-methylbenzo[b]thiophene-2-carboxylic acid methyl ester 5-Hydroxymethyl-3-methylbenzo[b]thiophene-2-carboxylic acid (4.44 g.) was dissolved in methanol (150 ml.) and the solution was saturated with hydrogen chloride gas. It was then heated under reflux for 4 hours and cooled. The solid which crystallized out was filtered off and dried. The product (3.54 g.) was shown by n.m.r. to consist of a mixture of 5-chloromethyl-3-methylbenzo[b]thiophene-2-carboxylic acid methyl ester (65%) and 5-methoxymethyl-3-methylbenzo[b]thiophene-2-carboxylic acid methyl ester. The product was chromatographed on silica gel. Elution with toluene first gave 5-chloromethyl-3-methylbenzo[b]thiophene-2-carboxylic acid methyl ester, m.p. 115°–116° C. (from petrol b.p. 40°–60° C.).

Analysis: Found: 56.60; H, 4.33. $C_{12}H_{11}ClO_2S$ Requires: 56.58; H, 4.35%.

Further elution with toluene gave 5-methoxymethyl-3-methylbenzo[b]thiophene-2-carboxylic acid methyl ester, m.p. 88°–89° C. (from petrol b.p. 40°–60° C.).

Analysis: Found: 62.42; H, 5.59. $C_{13}H_{14}O_3S$ Requires: 62.38; H, 5.64%.

(iv) 5-(1-Imidazolylmethyl)-3-methylbenzo[b]thiophene-2-carboxylic acid methyl ester

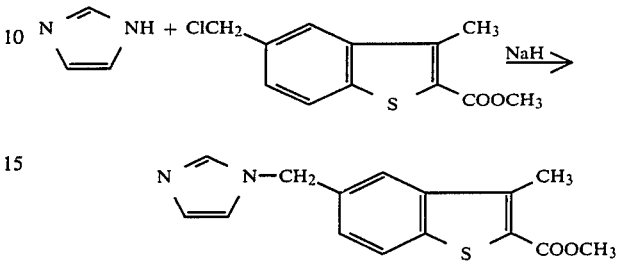

To a solution of imidazole (0.23 g.) in dry N,N-dimethylformamide (10 ml.) was added sodium hydride (0.17 g. of 50% dispersion in mineral oil) and the mixture was stirred for 30 minutes. A solution of 5-chloromethyl-3-methylbenzo[b]thiophene-2-carboxylic acid methyl ester (0.82 g.) in dry N,N-dimethylformamide (10 ml.) was then added dropwise with stirring and the resulting mixture was stirred at room temperature for 2.5 hours and then evaporated. The residue was poured into water and the mixture was extracted several times with ethyl acetate. The combined extracts were washed with water, dried ($Na_2SO_4$) and evaporated to give a solid which was chromatographed on silica gel. Elution with chloroform gave first some impurity followed by pure product. The product containing fractions were combined to give a solid which was crystallized from ethyl acetate/petrol (b.p. 60°–80°) to give 5-(1-imidazolylmethyl)-3-methylbenzo[b]thiophene-2-carboxylic acid methyl ester (0.30 g.), m.p. 136°–138°.

Analysis: Found: C, 62.43; H, 4.75; N, 9.99. Requires: C, 62.91; H, 4.92; N, 9.78%.

EXAMPLE 9

6-(1-Imidazolylmethyl)-3-methylbenzo[b]thiophene-2-carboxylic acid methyl ester

(i) 2-Bromo-6-hydroxymethyl-3-methylbenzo[b]thiophene

A solution of borane-tetrahydrofuran complex (150 ml. of 1M solution in THF) was added dropwise with stirring to a solution of 2-bromo-3-methylbenzo[b]thiophene-6-carboxylic acid (7.32 g.) in dry tetrahydrofuran (120 ml.) at 0° C. under an atmosphere of dry nitrogen. The solution was stirred at room temperature for 4 hours and then the excess borane was decomposed by the cautious addition of methanol. The solution was evaporated and the residue was dissolved in ether. The solution was washed with water, dried ($Na_2SO_4$) and evaporated to give a solid which was crystallized from ether/petrol (b.p. 40°–60°) to give 2-bromo-6-hydroxymethyl-3-methylbenzo[b]thiophene (5.70 g.), m.p. 91° C.

Analysis: Found: C, 46.90; H, 3.51. $C_{10}H_9BrOS$ Requires: C, 46.70; H, 3.53%.

(ii)
6-Hydroxymethyl-3-methylbenzo[b]thiophene-2-carboxylic acid

Treatment of 2-bromo-6-hydroxymethyl-3-methylbenzo[b]thiophene with n-butyl lithium and carbon dioxide according to the method of Example 8(ii) gave 6-hydroxymethyl-3-methylbenzo[b]thiophene-2-carboxylic acid, m.p. 234°–236° C. (from ethanol/water).

Analysis: Found: C, 59.28; H, 4.50. $C_{11}H_{10}O_3S$ Requires: C, 59.44; H, 4.54%.

(iii)
6-Hydroxymethyl-3-methylbenzo[b]thiophene-2-carboxylic acid methyl ester Treatment of the above acid with methanol in the presence of hydrogen chloride by the method of Example 8(iii) gave 6-hydroxymethyl-3-methylbenzo[b]thiophene-2-carboxylic acid methyl ester m.p. 121°–123° (from ethyl acetate/petrol b.p. 60°–80°).

Analysis: Found: C, 60.87; H, 5.16. $C_{12}H_{12}O_3S$ Requires: C, 60.99; H, 5.12%.

(iv)
6-Chloromethyl-3-methylbenzo[b]thiophene-2-carboxylic acid methyl ester Thionyl chloride (0.75 ml.) was added cautiously to a solution of 6-hydroxymethyl-3-methylbenzo[b]thiophene-2-carboxylic acid methyl ester (0.70 g.) and pyridine (3 drops) in chloroform (7.5 ml.) and the resulting solution was allowed to stand for 1 hour. It was then washed successively with water, sodium bicarbonate solution and dried ($Na_2SO_4$). Evaporation of the solvent gave a solid which was crystallized from petrol (b.p. 60°–80°) to give 6-chloromethyl-3-methylbenzo[b]thiophene-2-carboxylic acid methyl ester (0.63 g.), m.p. 128°–129° C.

Analysis: Found: C, 56.60; H, 4.34. $C_{12}H_{11}ClO_2S$ Requires: C, 56.58; H, 4.35%.

(v)
6-(1-Imidazolylmethyl)-3-methylbenzo[b]thiophene-2-carboxylic acid methyl ester

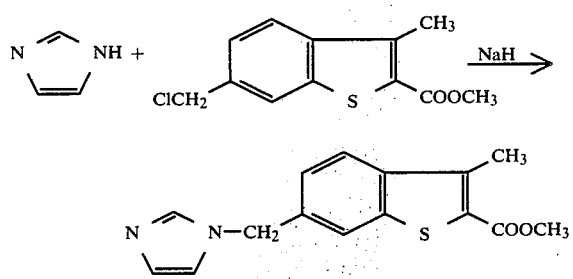

Successive treatment of imidazole with sodium hydride and 6-chloromethyl-3-methylbenzo[b]thiophene-2-carboxylic acid methyl ester by the method of Example 8(iv) gave 6-(1-imidazolylmethyl)-3-methylbenzo[b]thiophene-2-carboxylic acid methyl ester, m.p. 147°–148° (from ethyl acetate/petrol b.p. 60°–80°).

Analysis: Found: C, 62.62; H, 4.99; N, 9.58. $C_{15}H_{14}N_2O_2S$ Requires: C, 62.91; H, 4.93; N, 9.78%.

EXAMPLE 10
6-(1-Imidazolylmethyl)-4-methoxybenzo[b]thiophene-2-carboxylic acid methyl ester

(i) 6-Hydroxymethyl-4-methoxybenzo[b]thiophene

Reduction of 4-methoxybenzo[b]thiophene-6-carboxylic acid methyl ester with lithium aluminium hydride according to the method of Example 8(i) gave 6-hydroxymethyl-4-methoxybenzo[b]thiophene, m.p. 59.5°–60.5° (from ethyl acetate/petrol b.p. 60°–80°).

Analysis: Found: C, 61.46; H, 5.32. $C_{11}H_{10}O_4S$ Requires: C, 61.83; H, 5.19%.

(ii)
6-Hydroxymethyl-4-methoxybenzo[b]thiophene-2-carboxylic acid

Successive treatment of 6-hydroxymethyl-4-methoxybenzo[b]thiophene with n-butyl lithium and carbon dioxide according to the method of Example 8(ii) gave 6-hydroxymethyl-4-methoxybenzo[b]thiophene-2-carboxylic acid, m.p. 205°–208° (from isopropanol/petrol b.p. 60°–80°).

Analysis: Found: C, 55.28; H, 4.17. $C_{11}H_{10}O_4S$ Requires: C, 55.45; H, 4.23%.

(iii)
6-Hydroxymethyl-4-methoxybenzo[b]thiophene-2-carboxylic acid methyl ester Treatment of the above acid with methanol in the presence of hydrogen chloride by the method of Example 8(iii) gave 6-hydroxymethyl-4-methoxybenzo[b]thiophene-2-carboxylic acid methyl ester, m.p. 113°–114° (from ethyl acetate/petrol b.p. 60°–80°).

Analysis: Found: C, 56.98; H, 4.94. $C_{12}H_{12}O_4S$ Requires: C, 57.13; H, 4.79%.

(iv)
6-Chloromethyl-4-methoxybenzo[b]thiophene-2-carboxylic acid methyl ester Treatment of 6-hydroxymethyl-4-methoxybenzo[b]thiophene-2-carboxylic acid methyl ester with thionyl chloride in the presence of pyridine according to the method of Example 9(iv) gave 6-chloromethyl-4-methoxybenzo[b]thiophene-2-carboxylic acid methyl ester, m.p. 147°–148° (from ethyl acetate/petrol b.p. 60°–80°).

Analysis: Found: C, 53.29; H, 4.08. $C_{12}H_{11}ClO_3S$ Requires: C, 53.23; H, 4.10%.

(v)
6-(1-Imidazolylmethyl)-4-methoxybenzo[b]thiophene-2-carboxylic acid methyl ester

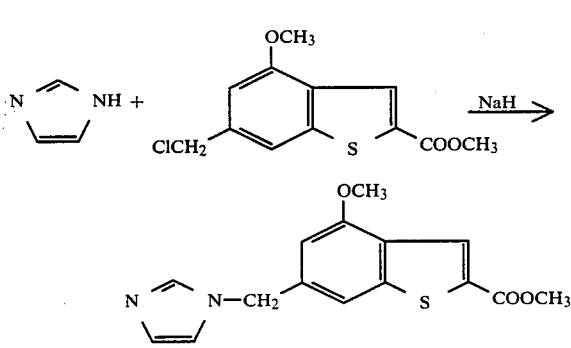

Successive treatment of imidazole with sodium hydride and 6-chloromethyl-4-methoxybenzo[b]thiophene-2-carboxylic acid methyl ester by the method of Example 8(iv) gave 6-(1-imidazolylmethyl)-4-methoxybenzo[b]thiophene-2-carboxylic acid methyl ester, m.p. 161°-162° (from ethyl acetate/petrol b.p. 60°-80°).

Analysis: Found: C, 59.27; H, 4.74; N, 9.56. $C_{15}H_{14}N_2O_3S$ Requires: C, 59.58; H, 4.67; N, 9.27%.

EXAMPLE 11

6-(1-Imidazolylmethyl)-2-methylbenzo[b]thiophene-3-carboxylic acid methyl ester (i)

3-Bromo-6-hydroxymethyl-2-methylbenzo[b]thiophene

Reduction of 3-bromo-2-methylbenzo[b]thiophene-6-carboxylic acid with borane-tetrahydrofuran complex according to the method of Example 9(i) gave 3-bromo-6-hydroxymethyl-2-methylbenzo[b]thiophene, m.p. 95°-96° C. (from chloroform/petrol b.p. 60°-80°).

Analysis: Found: 46.75; H, 3.55. $C_{10}H_9BrOS$ Requires: 46.70; H, 3.53%.

(ii)

6-Hydroxymethyl-2-methylbenzo[b]thiophene-3-carboxylic acid

A solution of 3-bromo-6-hydroxymethyl-2-methylbenzo[b]thiophene (2.11 g.) in dry ether (150 ml.) was added dropwise over 20 minutes to a stirred solution of n-butyl lithium (25 ml. of 1.5M solution in hexane) in dry ether (150 ml.) at −70° C. under an atmosphere of dry nitrogen. The mixture was stirred at −70° C. for 2 hours and then poured onto a mixture of crushed solid carbon dioxide and ether. When all the carbon dioxide had evaporated the mixture was shaken with water and the aqueous layer was separated and acidified with concentrated hydrochloric acid. The solid was filtered off, washed well with water and dried to give 6-hydroxymethyl-2-methylbenzo[b]thiophene-3-carboxylic acid (1.26 g.), m.p. 195°-196° C., raised to 196°-197° C. on crystallization from ethanol/water.

Analysis: Found: C, 59.25; H, 4.67. $C_{11}H_{10}O_3S$ Requires: C, 59.44; H, 4.54%.

(iii)

6-Chloromethyl-2-methylbenzo[b]thiophene-3-carboxylic acid methyl ester

The above acid (2.50 g.) was dissolved in methanol (100 ml.) and the solution was saturated with hydrogen chloride gas. The solution was heated under reflux for 3 hours and then evaporated. The residue was dissolved in ether and the solution was washed with sodium bicarbonate solution, water and dried ($Na_2SO_4$). Evaporation of the solvent gave an oil which was chromatographed on silica gel. Elution with toluene gave a solid which was crystallized from petrol (b.p. 60°-80°) to give 6-chloromethyl-2-methylbenzo[b]thiophene-3-carboxylic acid methyl ester, (0.51 g.), m.p. 78°-79° C.

Analysis: Found: C, 56.52; H, 4.36. $C_{11}H_{11}ClO_2S$ Requires: C, 56.58; H, 4.35%.

Further elution with toluene gave impure fractions which seemed to contain, according to n.m.r. evidence, increasing amounts of 6-methoxymethyl-2-methylbenzo[b]thiophene-3-carboxylic acid methyl ester. These fractions were not investigated further.

(iv)

6-(1-Imidazolylmethyl)-2-methylbenzo[b]thiophene-3-carboxylic acid methyl ester

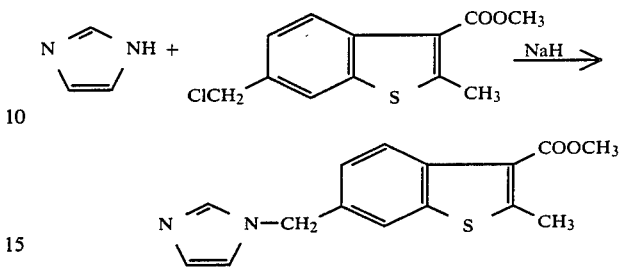

Successive treatment of imidazole with sodium hydride and 6-chloromethyl-2-methylbenzo[b]thiophene-3-carboxylic acid methyl ester by the method of Example 8(iv) gave 6-(1-imidazolylmethyl)-2-methylbenzo[b]thiophene-3-carboxylic acid methyl ester, m.p. 134°-135° C.

Accurate mass measurement M/e 286.0764. $C_{15}H_{14}N_2O_2S$ Requires: 286.0775.

EXAMPLE 12

6-[2-(1-Imidazolyl)ethyl]-2-methylbenzo[b]thiophene-3-carboxylic acid methyl ester (i)

3-Bromo-6-carboxymethyl-2-methylbenzo[b]thiophene

A mixture of 6-acetyl-3-bromo-2-methylbenzo[b]thiophene (12.0 g.), sulphur (3.0 g.) and morpholine (12 ml.) was heated under reflux for 6 hours. (This is the Willgerodt-Kindler reaction.) The mixture was poured into water and the resulting green solid was filtered off, washed with water and added to a solution of sodium hydroxide (12.0 g.) in methanol (250 ml.). The mixture was heated under reflux for 6.5 hours and then evaporated. The residue was dissolved in water and the solution was washed with ethyl acetate. The aqueous layer was acidified to give a solid which was filtered off, washed with water and dried to give 3-bromo-6-carboxymethyl-2-methylbenzo[b]thiophene (8.22 g.) pure enough for further reaction. A portion crystallized from toluene/petrol (b.p. 60°-80°) had m.p. 150°-152° C.

Analysis: Found: C, 45.92; H, 3.03. $C_{11}H_9BrO_2S$ Requires: C, 46.33; H, 3.18%.

(ii)

3-Bromo-6-(2-hydroxyethyl)-2-methylbenzo[b]thiophene

Reduction of 3-bromo-6-carboxymethyl-2-methylbenzo[b]thiophene with borane-tetrahydrofuran complex by the method of Example 9(i) gave 3-bromo-6-(2-hydroxyethyl)-2-methylbenzo[b]thiophene, m.p. 69°-70° C.

Analysis: Found: C, 48.80; H, 4.09. $C_{11}H_{11}BrOS$ Requires: C, 48.72; H, 4.15%.

(iii)

6-(2-Hydroxyethyl)-2-methylbenzo[b]thiophene-3-carboxylic acid

Successive treatment of 3-bromo-6-(2-hydroxyethyl)-2-methylbenzo[b]thiophene with n-butyl lithium in ether followed by carbon dioxide according to the method of Example 11(ii) gave 6-(2-hydroxyethyl)-2- methylbenzo[b]thiophene-3-carboxylic acid, m.p. 166°–169° C. (from toluene).

Analysis: Found: C, 60.83; H, 4.95. $C_{12}H_{12}O_3S$ Requires: C, 60.99; H, 5.12%.

(iv) 6-(2-Hydroxyethyl)-2-methylbenzo[b]thiophene-3-carboxylic acid methyl ester Treatment of the above acid with methanol in the presence of hydrogen chloride by the method of Example 8(iii) gave 6-(2-hydroxyethyl)-2-methylbenzo[b]thiophene-3-carboxylic acid methyl ester which was used directly in the next stage.

(v) 6-(2-Methanesulphonyloxyethyl)-2-methylbenzo[b]thiophene-3-carboxylic acid methyl ester Methanesulphonyl chloride (0.69 g.) was added dropwise to a stirred solution of the above ester (0.51 g.) and triethylamine (0.61 g.) in dry methylene chloride (20 ml.) at 0° C. and the resulting mixture was stirred at 0° C. for 15 minutes. It was then washed with water, dried ($Na_2SO_4$) and evaporated to give 6-(2-methanesulphonyloxyethyl)-2-methylbenzo[b]thiophene-3-carboxylic acid methyl ester (0.65 g.) which was used directly in the next stage.

(vi) 6-[2-(1-Imidazolyl)ethyl]-2-methylbenzo[b]thiophene-3-carboxylic acid methyl ester

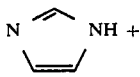

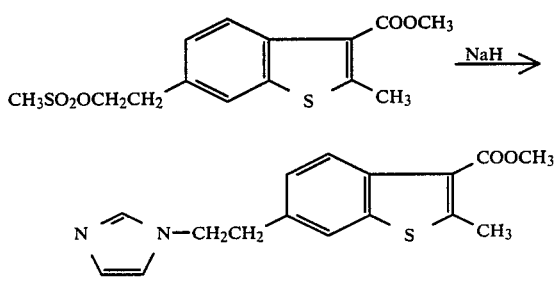

Successive treatment of imidazole with sodium hydride and 6-(2-methanesulphonyloxyethyl)-2-methylbenzo[b]thiophene-3-carboxylic acid methyl ester according to the method of Example 8(iv) gave a crude product which was chromatographed on silica gel. Elution with chloroform gave first a low melting solid identified as 2-methyl-6-vinylbenzo[b]thiophene-3-carboxylic acid methyl ester.

Accurate mass measurement M/e 232.0547.
$C_{13}H_{12}O_2S$ Requires: 232.0557.

Further elution with chloroform gave 6-[2-(1-imidazolyl)ethyl]-2-methylbenzo[b]thiophene-3-carboxylic acid methyl ester, m.p. 90°–92°.

Accurate mass measurement M/e 300.0926.
$C_{16}H_{16}N_2O_2S$ Requires: 300.0932.

EXAMPLE 13
5-[2-(1-Imidazolyl)ethoxy]benzo[b]thiophene-2-carboxylic acid methyl ester

(i) 5-(2-Chloroethoxy)benzo[b]thiophene-2-carboxylic acid methyl ester

5-Hydroxybenzo[b]thiophene-2-carboxylic acid methyl ester (1.47 g.) was dissolved in a solution of sodium (0.163 g.) in methanol (15 ml.) and 2-(benzenesulphonyloxy)ethyl chloride (1.57 g.) was added. The resulting solution was heated under reflux for 8 hours and then allowed to cool and stood overnight. The solution was then evaporated and the residue was partitioned between water and ether. The aqueous layer was separated and washed several times with ether. The combined organic layer and ethereal extracts were washed with water, dried ($Na_2SO_4$) and evaporated. The residue was chromatographed on silica gel. Elution with chloroform gave a solid which was crystallized from ethyl acetate/petrol (b.p. 60°–80°) to give 5-(2-chloroethoxy)benzo[b]thiophene-2-carboxylic acid methyl ester, (0.74 g.), m.p. 116°–117° C.

Analysis: Found: C, 53.31; H, 4.00. $C_{12}H_{11}ClO_3S$ Requires: C, 53.23; H, 4.10%.

(ii) 5-[2-(1-Imidazolyl)ethoxy]benzo[b]thiophene-2-carboxylic acid methyl ester

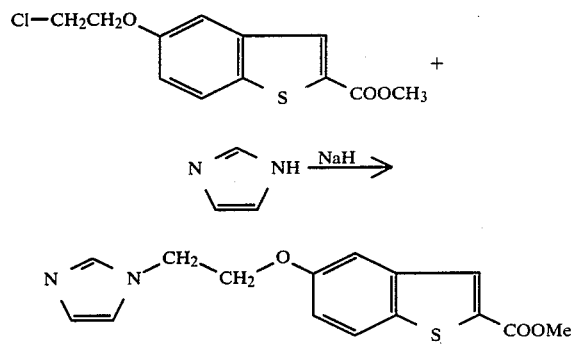

Sodium hydride (0.22 g. of 50% dispersion in mineral oil) was added portionwise with stirring to a solution of imidazole (0.306 g.) in dry N,N-dimethylformamide (10 ml.) and the mixture was stirred at room temperature for 30 minutes and then warmed for a few minutes. 5-(2-Chloroethoxy)benzo[b]thiophene-2-carboxylic acid methyl ester (1.22 g.) was then added and the mixture was heated on a steam bath for 5 hours, and then cooled and poured into water. The mixture was extracted several times with ethyl acetate and the combined extracts were washed well with water and dried ($Na_2SO_4$). Evaporation of the solvent gave an oil which was chromatographed on silica gel. Elution with chloroform gave first mineral oil and some impurity followed by pure product. The product containing fractions were evaporated to give a solid which was crystallized from ethyl acetate/petrol (b.p. 60°–80°) to give 5-[2-(1-imidazolyl)ethoxy]benzo[b]thiophene-2-carboxylic acid methyl ester (0.45 g.), m.p. 127°–129° C.

Analysis: Found: C, 59.93; H, 4.65; N, 9.29. $C_{15}H_{14}N_2O_3S$ Requires: C, 59.58; H, 4.67; N, 9.27%.

EXAMPLE 14

6-[2-(1-Imidazolyl)ethoxy]-3-methylbenzo[b]thiophene-2-carboxylic acid methyl ester (i) 6-Methoxy-3-methylbenzo[b]thiophene-2-carboxylic acid methyl ester A solution of 6-methoxy-3-methylbenzo[b]thiophene-2-carboxylic acid (7.50 g.) in methanol (400 ml.) was saturated with hydrogen chloride gas and the solution was heated under reflux for 2 hours and then evaporated. The residue was dissolved in ethyl acetate and the solution was washed successively with water, sodium bicarbonate solution, water and dried ($Na_2SO_4$). Evaporation of the solvent gave a solid which was crystallized from methanol to give 6-methoxy-3-methylbenzo[b]thiophene-2-carboxylic acid methyl ester (5.59 g.), m.p. 118°–120° C.

Analysis: Found: C, 60.87; H, 5.08. $C_{12}H_{12}O_3S$ Requires: C, 60.99; H, 5.12%.

(ii) 6-Hydroxy-3-methylbenzo[b]thiophene-2-carboxylic acid methyl ester

Boron tribromide (5.0 ml.) was added dropwise to a stirred solution of 6-methoxy-3-methylbenzo[b]thiophene-2-carboxylic acid methyl ester (4.70 g.) in dry methylene chloride (200 ml.) at −78° C. and the resulting suspension was stirred at −78° for 15 minutes followed by 24 hours at room temperature. The mixture was then treated cautiously with methanol and the solution was washed with sodium bicarbonate solution. The organic layer was dried ($Na_2SO_4$) and evaporated to give a solid which was chromatographed on silica gel. Elution with chloroform first gave a trace of impurity followed by pure product. The product-containing fractions were evaporated to give a solid which was crystallized from ethyl acetate/petrol (b.p. 60°–80°) to give 6-hydroxy-3-methylbenzo[b]thiophene-2-carboxylic acid methyl ester (3.58 g.), m.p. 174°–176°.

Analysis: Found: C, 59.83; H, 4.52. $C_{11}H_{10}O_3S$ Requires: C, 59.44; H, 4.54%.

(iii) 6-(2-Chloroethoxy)-3-methylbenzo[b]thiophene-2-carboxylic acid methyl ester Treatment of 6-hydroxy-3-methylbenzo[b]thiophene-2-carboxylic acid methyl ester with 2-(benzenenesulphonyloxy)ethyl chloride according to the method of Example 13(i) gave 6-(2-chloroethoxy)-3-methylbenzo[b]thiophene-2-carboxylic acid methyl ester, m.p. 131°–132° (from ethyl acetate/petrol b.p. 60°–80°).

Analysis: Found: C, 55.07; H, 4.58. $C_{13}H_{13}ClO_3S$ Requires: C, 54.83; H, 4.60%.

(iv) 6-[2-(1-Imidazolyl)ethoxy]-3-methylbenzo[b]thiophene-2-carboxylic acid methyl ester

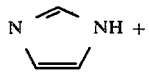

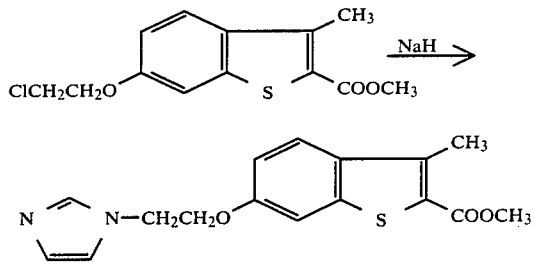

Successive treatment of imidazole with sodium hydride and 6-(2-chloroethoxy)-3-methylbenzo[b]thiophene-2-carboxylic acid methyl ester according to the method of Example 13(ii) gave 6-[2-(1-imidazolyl)ethoxy]-3-methylbenzo[b]thiophene-2-carboxylic acid methyl ester, m.p. 162°–163° C. (from ethyl acetate/petrol b.p. 60°–80°).

Analysis: Found: C, 60.77; H, 5.10; N, 8.68. $C_{16}H_{16}N_2O_3S$ Requires: C, 60.74; H, 5.10; N, 8.86%.

EXAMPLE 15

5-(3-Pyridyloxymethyl)benzo[b]thiophene-2-carboxylic acid methyl ester

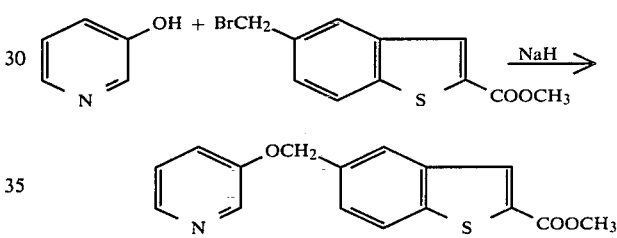

3-Hydroxypyridine (0.40 g.) was dissolved in dry N,N-dimethylformamide (10 ml.) and sodium hydride (0.20 g. of 50% dispersion in mineral oil) was added portionwise with stirring and the resulting mixture was stirred at room temperature for 30 minutes. 5-(Bromomethyl)benzo[b]thiophene-2-carboxylic acid methyl ester (1.20 g.) in a few mls of dry N,N-dimethylformamide was then added and the mixture was stirred at room temperature for 30 minutes, and then poured into water. The mixture was extracted several times with ethyl acetate and the combined extracts were washed well with water and dried ($Na_2SO_4$). Evaporation of the solvent gave an oil which was chromatographed on silica gel. Elution with a mixture of chloroform and toluene (1:1) first gave mineral oil followed by pure product. Evaporation of the product-containing fractions gave a solid (0.40 g.) which was crystallized from isopropanol/petrol (b.p. 60°–80°) to give 5-(3-pyridyloxymethyl)benzo[b]thiophene-2-carboxylic acid methyl ester, m.p. 106°–107° C.

Analysis: Found: C, 63.98; H, 4.39; N, 4.66. $C_{16}H_{13}NO_3S$ Requires: C, 64.21; H, 4.38; N, 4.68%.

EXAMPLES 16–20

Other (3-pyridyloxymethyl)benzo[b]thiophene-2-carboxylic acid esters were prepared similarly to Example 15 from 3-hydroxypyridine and the appropriate chloro- or bromo-methylbenzo[b]thiophene ester [prepared as described in the previous examples]. The compounds are listed in Table 4.

TABLE 4

| | Structure | m.p. °C. | Recrystn. Solvent | Analysis |
|---|---|---|---|---|
| 16 | | 126–127 | Methanol/H₂O | Found: C, 63.80; H, 4.40; N, 4.60. $C_{16}H_{13}NO_3S$ Requires: C, 64.20; H, 4.38; N, 4.68%. |
| 17 | | 104–105 | Ethyl acetate/ petrol (b.p. 60–80°) | Found: C, 64.96; H, 4.97; N, 4.39. $C_{17}H_{15}NO_3S$ Requires: C, 65.15; H, 4.83; N, 4.47%. |
| 18 | | 139–141 | Ethyl acetate/ petrol (b.p. 60–80°) | Found: C, 57.20; H, 3.63; N, 4.15. $C_{16}H_{12}ClNO_3S$ Requires: C, 56.89; H, 3.58; N, 4.15%. |
| 19 | | 133–134 | Ethyl acetate/ petrol (b.p. 60–80°) | Found: C, 64.12; H, 4.57; N, 4.50. $C_{16}H_{13}NO_3S$ Requires: C, 64.20; H, 4.38; N, 4.68%. |
| 20 | | 80–81 | Ether/petrol (b.p. 40–60°) | Found: C, 63.69; H, 4.40; N, 4.74. $C_{16}H_{13}NO_3S$ Requires: C, 64.20; H, 4.38; N, 4.68%. |

EXAMPLE 21

5-(3-Pyridylmethoxy)benzo[b]thiophene-2-carboxylic acid methyl ester

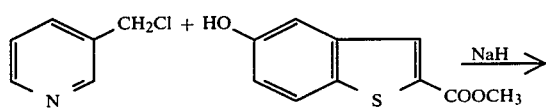

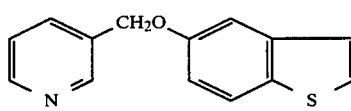

Sodium hydride (0.24 g. of 50% dispersion in mineral oil) was added portionwise to a solution of 5-hydroxybenzo[b]thiophene-2-carboxylic acid methyl ester (1.04 g.) in dry N,N-dimethylformamide (10 ml.) and the mixture was stirred at room temperature for 30 minutes. 3-Chloromethylpyridine (0.65 g.) in dry N,N-dimethylformamide (5 ml.) was then added and the mixture was stirred at room temperature for 1 hour, and then poured into water. The mixture was extracted several times with ethyl acetate and the combined extracts were washed well with water and dried (Na₂SO₄). Evaporation of the solvent gave a solid which was washed with petrol and crystallized from isopropanol to give 5-(3-pyridylmethoxy)benzo[b]thiophene-2-carboxylic acid methyl ester (0.80 g.), m.p. 126°–127° C.

Analysis: Found: C, 63.87; H, 4.38; N, 4.46. $C_{16}H_{13}NO_3S$ Requires: C, 64.19; H, 4.38; N, 4.68%.

EXAMPLE 22

3-Methyl-6-(3-pyridylmethoxy)benzo[b]thiophene-2-carboxylic acid methyl ester

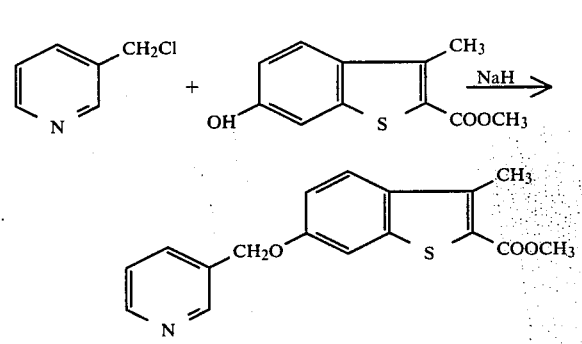

Successive treatment of 6-hydroxy-3-methylbenzo[b]thiophene-2-carboxylic acid methyl ester [prepared as described in Example 14(ii)] with sodium hydride and 3-chloromethylpyridine by the method of Example 21 gave 3-methyl-6-(3-pyridylmethoxy)benzo[b]thiophene-2-carboxylic acid methyl ester, m.p. 110°-112° C. (from ethyl acetate/petrol b.p. 60°-80°).

Analysis: Found: C, 65.00; H, 4.81; N, 4.32. $C_{17}H_{15}NO_3S$ Requires: C, 65.15; H, 4.83; N, 4.47%.

EXAMPLE 23

E-6-[2-(3-Pyridylvinyl)]-3-methylbenzo[b]thiophene-2-carboxylic acid methyl ester

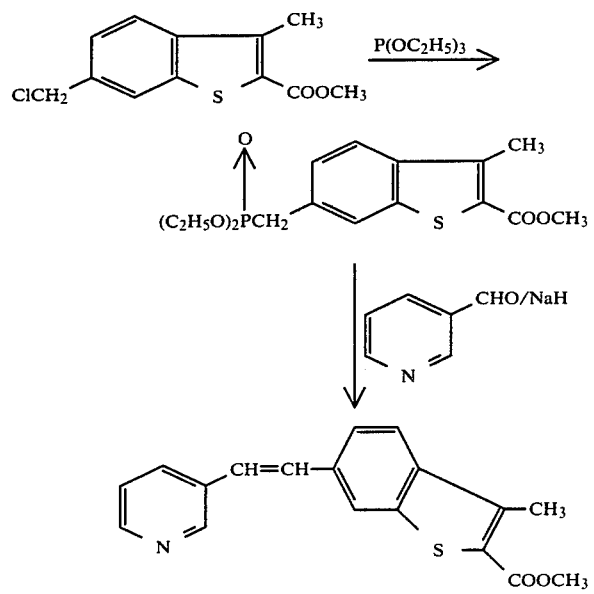

A mixture of 6-chloromethyl-3-methylbenzo[b]thiophene-2-carboxylic acid methyl ester (0.50 g.) and triethyl phosphite (1.0 ml.) was heated under reflux for 3 hours and then the excess of triethyl phosphite was distilled off. The solid residue was dissolved in dry dimethoxyethane (10 ml.) and sodium hydride (0.11 g. of 50% dispersion in mineral oil) was added. The mixture was stirred at room temperature for 1 hour and then pyridine-3-carboxaldehyde (0.21 g.) was added. The mixture was stirred for 3 hours, allowed to stand for 18 hours and then evaporated. Water was added to the residue followed by ethyl acetate and the mixture was shaken. The aqueous layer was separated and washed with two further portions of ethyl acetate. The combined extracts were dried ($Na_2SO_4$) and evaporated to give a solid which was chromatographed on silica gel. Elution with chloroform gave E-6-[2-(3-pyridylvinyl)]-3-methylbenzo[b]thiophene-2-carboxylic acid methyl ester (0.12 g.), m.p. 114°-115° C.

Analysis: Found: C, 69.80; H, 4.93; N, 4.46. $C_{18}H_{15}NO_2S$ Requires: C, 69.88; H, 4.89; N, 4.53%.

EXAMPLE 24

E-5-[2-(4-Pyridylvinyl)]-3-methylbenzo[b]thiophene-2-carboxylic acid ethyl ester (i) 5-Bromo-3-methylbenzo[b]thiophene-2-carboxylic acid A mixture of diisopropylamine (4.44 g.) and potassium t-butoxide (5.02 g.) in dry ether was cooled to −78° C. under an atmosphere of dry nitrogen and n-butyl lithium (28.4 ml. of 1.55M solution in hexane) was added with stirring over 5 minutes. The mixture was stirred at −78° for 30 minutes and then a solution of 5-bromo-3-methylbenzo[b]thiophene (9.10 g.) in dry ether (25 ml.) was added over 5 minutes. The resulting mixture was stirred at −78° C. for 30 minutes and then poured onto a mixture of crushed solid carbon dioxide and ether. When all the carbon dioxide had evaporated the mixture was shaken with water and the ether layer was separated. The aqueous layer was acidified with acetic acid and the solid was filtered off, washed with water and crystallized from acetic acid to give 5-bromo-3-methylbenzo[b]thiophene-2-carboxylic acid (7.30 g.), m.p. >300°.

Analysis: Found: C, 44.77; H, 2.76. $C_{10}H_7BrO_2S$ Requires: C, 44.29; H, 2.60%.

(ii) 5-Bromo-3-methylbenzo[b]thiophene-2-carboxylic acid ethyl ester

A mixture of 5-bromo-3-methylbenzo[b]thiophene-2-carboxylic acid (5.80 g.), ethanol (500 ml.) and concentrated sulphuric acid (2 ml.) was heated under reflux for 48 hours, and then evaporated. Dilute aqueous ammonia solution was added and the solid was filtered off, washed well with water and dried to give 5-bromo-3-methylbenzo[b]thiophene-2-carboxylic acid ethyl ester (5.70 g.), m.p. 87°-88° C., raised to 88°-89° on crystallization from petrol (b.p. 80°-100°).

Analysis: Found: C, 47.75; H, 3.64. $C_{12}H_{11}BrO_2S$ Requires: C, 48.17; H, 3.71%.

(iii)
E-5-[2-(4-Pyridylvinyl)]-3-methylbenzo[b]thiophene-2-carboxylic acid ethyl ester

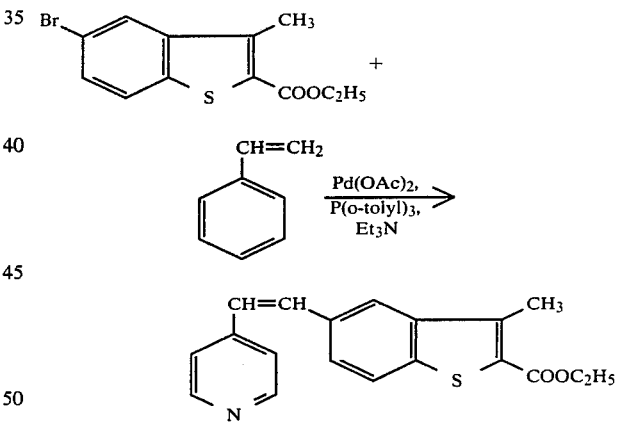

A mixture of 5-bromo-3-methylbenzo[b]thiophene-2-carboxylic acid methyl ester (1.00 g.), 4-vinylpyridine (0.42 g.), palladous acetate (0.01 g.), tri-o-tolylphosphine (0.03 g.) and triethylamine (4 ml.) was heated at 100° C. under an atmosphere of nitrogen for 16 hours. The mixture was cooled, water (20 ml.) was added and the mixture was extracted several times with ethyl acetate. The combined extracts were washed with water and dried ($Na_2SO_4$). Evaporation of the solvent gave a solid which was chromatographed on silica gel. Elution with chloroform gave first some impurity followed by pure product. The product-containing fractions were evaporated and the residue was crystallized from ethyl acetate/petrol (b.p. 60°-80°) to give E-5-[2-(4-pyridylvinyl)]-3-methylbenzo[b]thiophene-2-carboxylic acid ethyl ester (0.63 g.), m.p. 137°-140° C.

Analysis: Found: C, 70.79; H, 5.37; N, 4.16. C₁₉H₁₇NO₂S Requires: C, 70.56; H, 5.30; N, 4.33%.

EXAMPLE 25

5-[2-(4-Pyridylethyl)]-3-methylbenzo[b]thiophene-2-carboxylic acid ethyl ester

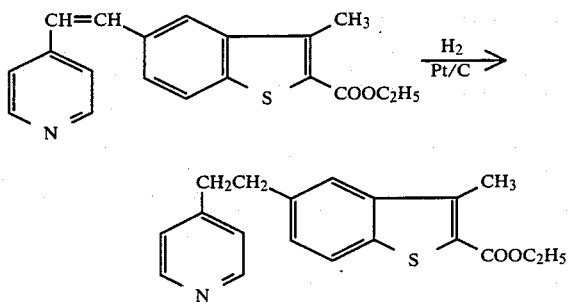

A solution of E-5-[2-(4-pyridylvinyl)]-3-methylbenzo[b]thiophene-2-carboxylic acid ethyl ester (0.50 g.) in ethanol (20 ml.) containing 5% platinum on carbon (0.05 g.) was hydrogenated at 50° C. and 4 atmospheres. When the required amount of hydrogen had been taken up the catalyst was filtered off and the solution was evaporated to give a solid which was crystallized from ethyl acetate/petrol (b.p. 60°-80°) to give 5-[2-(4-pyridylethyl)]-3-methylbenzo[b]thiophene-2-carboxylic acid ethyl ester (0.30 g.), m.p. 98°-100° C.

Analysis: Found: C, 70.45; H, 5.98; N, 4.41. C₁₉H₁₉NO₂S Requires: C, 70.12; H, 5.88; N, 4.30%.

EXAMPLE 26

5-(1-Imidazolylmethyl)benzofuran-2-carboxylic acid methyl ester (i) 5-Bromomethylbenzofuran-2-carboxylic acid methyl ester Treatment of 5-methylbenzofuran-2-carboxylic acid methyl ester with N-bromosuccinimide according to the method of Example 1(ii) gave 5-bromomethylbenzofuran-2-carboxylic acid methyl ester, m.p. 107°-109° (from ether/petrol b.p. 40°-60°) which was used directly in the next stage.

(ii) 5-(1-Imidazolylmethyl)benzofuran-2-carboxylic acid methyl ester

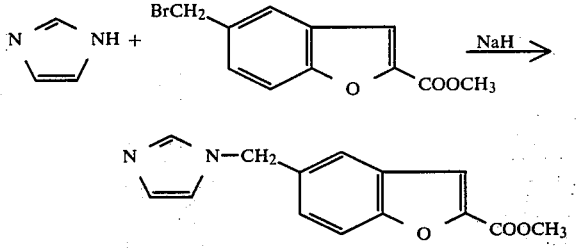

Successive treatment of imidazole with sodium hydride and 5-bromomethylbenzofuran-2-carboxylic acid methyl ester according to the method of Example 1(iii) gave 5-(1-imidazolylmethyl)benzofuran-2-carboxylic acid methyl ester, m.p. 146°-147° C. (from ethyl acetate/petrol b.p. 60°-80°).

Analysis: Found: C, 65.35; H, 4.75; N, 10.70. C₁₄H₁₂N₂O₃ Requires: C, 65.62; H, 4.72; N, 10.93%.

EXAMPLE 27

6-(1-Imidazolylmethyl)benzofuran 2-carboxylic acid methyl ester (i) 6-Bromomethylbenzofuran-2-carboxylic acid methyl ester Treatment of 6-methylbenzofuran-2-carboxylic acid methyl ester with N-bromosuccinimide according to the method of Example 1(iii) gave 6-bromomethylbenzofuran-2-carboxylic acid methyl ester, m.p. 117°-119° (from ethyl acetate/petrol b.p. 60°-80°).

Analysis: Found: C, 49.02; H, 3.26. C₁₁H₉BrO₃ Requires: C, 49.09; H, 3.37%.

(ii) 6-(1-Imidazolylmethyl)benzofuran-2-carboxylic acid methyl ester

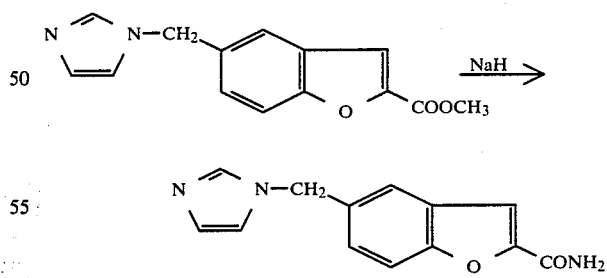

Successive treatment of imidazole with sodium hydride and 6-bromomethylbenzofuran-2-carboxylic acid methyl ester according to the method of Example 1(iii) gave 6-(1-imidazolylmethyl)benzofuran-2-carboxylic acid methyl ester, m.p. 172°-174° (from ethyl acetate).

Analysis: Found: C, 65.95; H, 4.74; N, 10.71. C₁₄H₁₂N₂O₃ Requires: C, 65.62; H, 4.72; N, 10.93%.

EXAMPLE 28

5-(1-Imidazolylmethyl)benzofuran-2-carboxamide

A solution of 5-(1-imidazolylmethyl)benzofuran-2-carboxylic acid methyl ester in a concentrated solution of ammonia in ethanol (25 ml.) was stirred for 18 hours and then evaporated. The residue was crystallized from isopropanol to give 5-(1-imidazolylmethyl)benzofuran-2-carboxamide (0.60 g.), m.p. 174°-176° C.

Analysis: Found: C, 64.35; H, 4.65; N, 17.75. C₁₃H₁₁N₃O₂ Requires: C, 64.7; H, 4.6; N, 17.4%.

EXAMPLE 29

7-(3-Pyridylmethoxy)benzofuran-2-carboxylic acid methyl ester (i) 7-Hydroxybenzofuran-2-carboxylic acid methyl ester Treatment of 7-hydroxybenzofuran-2-carboxylic acid with methanol in the presence of hydrogen chloride according to the method of Example 1(i) gave 7-hydroxybenzofuran-2-carboxylic acid methyl ester, m.p. 159°–160° (from methanol).

Analysis: Found: C, 62.30; H, 4.33. $C_{10}H_8O_4$ Requires: C, 62.50; H, 4.20%.

(ii) 7-(3-Pyridylmethoxy)benzofuran-2-carboxylic acid methyl ester

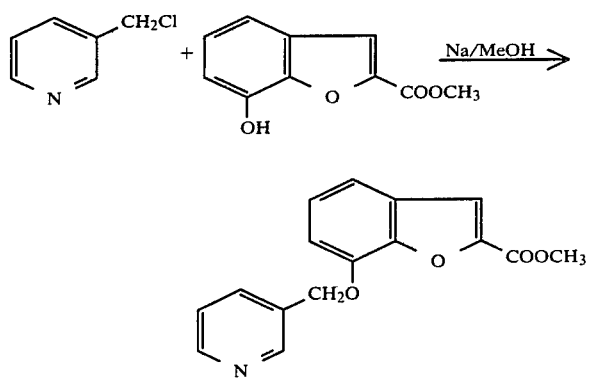

Sodium (0.37 g.) was dissolved in methanol (70 ml.) and 7-hydroxybenzofuran-2-carboxylic acid methyl ester (1.54 g.) was added. The solution was stirred for 15 minutes ad then 3-chloromethylpyridine hydrochloride (1.32 g.) was added. The mixture was heated under reflux for 8 hours and then evaporated. Water was added to the residue and the mixture was extracted sevral times with ethyl acetate. The combined extracts were washed with water and dried ($Na_2SO_4$). Evaporation of the solvent gave a solid which was chromatographed on silica gel. Elution with chloroform gave a solid which was crystallized from methanol/water to give 7-(3-pyridylmethoxy)benzofuran-2-carboxylic acid methyl ester (1.0 g.), m.p. 117°–118° C.

Analysis: Found: C, 67.50; H, 4.78; N, 5.17. $C_{16}H_{13}NO_4$ Requires: C, 67.84; H, 4.63; N, 4.95%.

EXAMPLE 30

7-(3-Pyridylmethoxy)benzofuran-2-carboxamide

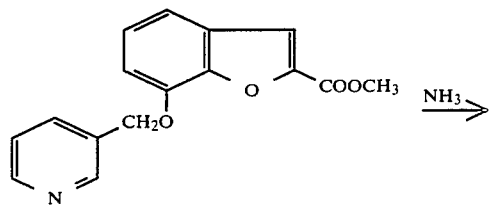

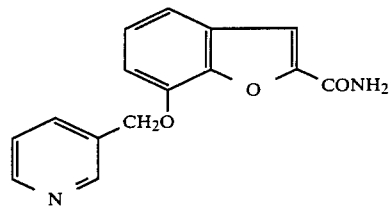

Treatment of 7-(3-pyridylmethoxy)benzofuran-2-carboxylic acid methyl ester with ethanolic ammonia according to the method of Example 28 gave 7-(3-pyridylmethoxy)benzofuran-2-carboxamide, m.p. 178°–179° C. (from methanol/water).

Analysis: Found: C, 66.60; H, 4.61; N, 10.29. $C_{15}H_{12}N_2O_3$ Requires: C, 67.15; H, 4.51; N, 10.44%.

EXAMPLE 31

6-(1-Imidazolylmethyl)indole-2-carboxylic acid methyl ester (i) 6-Methylindole-2-carboxylic acid methyl ester A solution of 6-methylindole-2-carboxylic acid (38.2 g.) in methanol (400 ml.) containing phosphorus oxychloride (5 ml.) was heated under reflux for 4 hours and then evaporated. The residue was dissolved in chloroform and the solution was washed successively with water and sodium bicarbonate solution and then dried ($Na_2SO_4$). Evaporation of the solvent gave a solid which was crystallized from methanol to give 6-methylindole-2-carboxylic acid methyl ester (28.1 g.), m.p. 128°–131° C.

Analysis: Found: C, 69.62; H, 5.80; N, 7.65. $C_{11}H_{11}NO_2$ Requires: C, 69.82; H, 5.86; N, 7.40%.

(ii) 1-Acetyl-6-methylindole-2-carboxylic acid methyl ester

Sodium hydride (4.70 g. of 50% dispersion in mineral oil) was added portionwise with stirring to a stirred solution of 6-methylindole-2-carboxylic acid methyl ester (18.0 g.) in dry N,N-dimethylformamide (100 ml.) and the mixture was stirred at room temperature for 1.5 hours. Acetyl chloride (8.0 g.) was then added dropwise with stirring and cooling and the resulting mixture was stirred at room temperature for 5 hours and then poured into water. The mixture was extracted several times with ethyl acetate and the combined extracts were washed with water and dried ($Na_2SO_4$). Evaporation of the solvent gave an oil which was chromatographed on silica gel. Elution with chloroform first gave mineral oil followed by pure product. Evaporation of the product-containing fractions gave a solid which are crystallized from methanol to give 1-acetyl-6-methylindole-2-carboxylic acid methyl ester (14.4 g.), m.p. 51°–53° C.

Analysis: Found: C, 67.57; H, 5.73; N, 6.30. $C_{13}H_{13}NO_3$ Requires: C, 67.52; H, 5.67; N, 6.06%.

(iii) 1-Acetyl-6-bromomethylindole-2-carboxylic acid methyl ester

Treatment of 1-acetyl-6-methylindole-2-carboxylic acid with N-bromosuccinimide by the method of Example 1(ii) gave 1-acetyl-6-bromomethylindole-2-carboxylic acid methyl ester, m.p. 93°–95° C. (from petrol b.p. 60°–80°).

Analysis: Found: C, 50.16; H, 3.71; N, 4.53. $C_{13}H_{12}BrNO_3$ Requires: C, 50.34; H, 3.90; N, 4.52 %.

(iv) 6-(1-Imidazolylmethyl)indole-2-carboxylic acid methyl ester

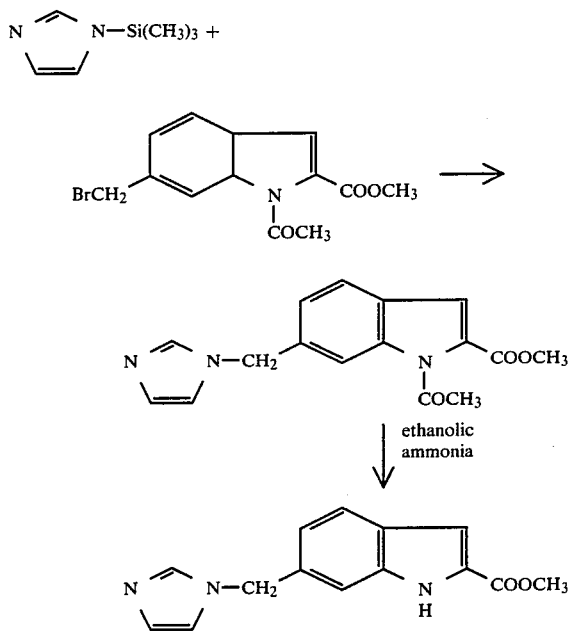

A solution of 1-acetyl-6-bromomethylindole-2-carboxylic acid methyl ester (3.1 g.) in toluene (25 ml.) was added dropwise with stirring to a solution of 1-trimethylsilylimidazole (5.60 g.) in toluene (25 ml.) at 80° C. The mixture was stirred at 80° for 2 hours and then evaporated. Water was added and the mixture was extracted several times with ethyl acetate. The combined extracts were washed with water, dried ($Na_2SO_4$) and evaporated to give an oil which was dissovled in a concentrated solution of ammonia in ethanol (40 ml.). The solution was allowed to stand at room temperature for 2.5 hours and then evaporated and the residue was chromatographed on silica gel. Elution with chloroform gave a solid which was crystallized from ethyl acetate to give 6-(1-imidazolylmethyl)indole-2-carboxylic acid methyl ester (1.49 g.), m.p. 204°–205° C.

Analysis: Found: C, 65.76; H, 5.16; N, 16.24. $C_{14}H_{13}N_3O_2$ Requires: C, 65.87; H, 5.13; N, 16.46%.

EXAMPLE 32

1-Benzyl-6-(1-imidazolylmethyl)indole-2-carboxylic acid methyl ester

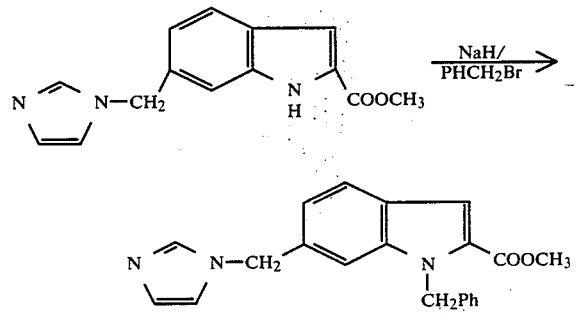

Sodium hydride (0.17 g. of 50% dispersion in mineral oil) was added portionwise to a stirred solution of 6-(1-imidazolylmethyl)indole-2-carboxylic acid methyl ester (0.90 g.) in dry N,N-dimethylformamide (50 ml.) and the mixture was stirred at room temperature for 1 hour. Benzyl bromide (0.61 g.) was added and the resulting mixture was stirred for 2 hours and then poured into water. The mixture was extracted several times with ethyl acetate and the combined extracts were washed well with water and dried ($Na_2SO_4$). Evaporation of the solvent gave an oil which was chromatographed on silica gel. Elution with chloroform first gave mineral oil followed by pure product. Evaporation of the product-containing fractions gave a solid which was crystallized from ethyl acetate/petrol (b.p. 60°–80°) to give 1-benzyl-6-(1-imidazolylmethyl)indole-2-carboxylic acid methyl ester, m.p. 120°–122° C.

Analysis: Found: C, 72.86; H, 5.52; N, 12.19. $C_{21}H_{19}N_3O_2$ Requires: C, 73.02; H, 5.54; N, 12.17%.

EXAMPLE 33

6-(1-Imidazolylmethyl)-3-methylbenzo[b]thiophene-2-carboxylic acid

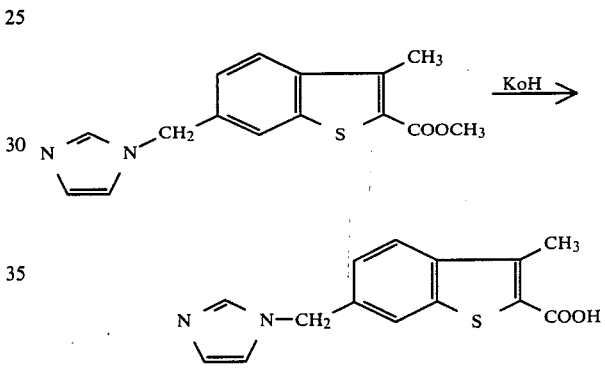

A mixture of 6-(1-imidazolylmethyl)-3-methylbenzo[b]thiophene-2-carboxylic acid methyl ester (0.25 g.) potassium hydroxide (0.10 g.), water (2.5 ml.) and methanol (2.5 ml.) was heated under reflux for 1 hour and then evaporated to small bulk. The solution was acidified with acetic acid and the solid was filtered off and dissolved in a slight excess of diluted potassium hydroxide solution. The solution was filtered and the filtrate was acidified. The solid was filtered off, washed with water and dried to give 6-(1-imidazolylmethyl)-3-methylbenzo[b]-thiophene-2-carboxylic acid (0.20 g.), m.p. 277°–278° C.

Analysis: Found: C, 61.50; H, 4.54; N, 10.39. $C_{14}H_{12}N_2O_2S$ Requires: C, 61.52; H, 4.42; N, 10.25%.

EXAMPLE 34

5-[2-(1-Imidazolyl)ethoxy]benzo[b]thiophene-2-carboxylic acid hydrochloride hemihydrate

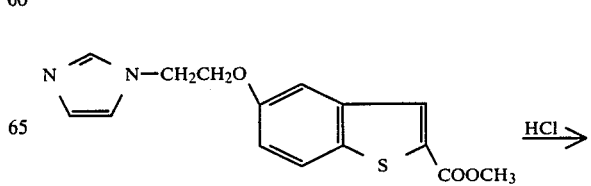

-continued

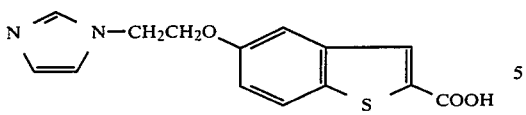

A mixture of 5-[2-(1-imidazolyl)ethoxy]benzo[b]thiophene-2-carboxylic acid methyl ester (0.35 g.) and concentrated hydrochloric acid (5 ml.) was heated on a steam bath for 5 hours and then evaporated. The residue was crystallized twice from ethanol/ether to give 5-[2-(1-imidazolyl)ethoxy]benzo[b]-thiophene-2-carboxylic acid hydrochloride hemihydrate (0.23 g.), m.p. 255°–258° C.

Analysis: Found: C, 50.01; H, 4.06; N, 8.16. $C_{14}H_{12}N_2O_3S.HCl.0.5H_2O$ Requires: C, 50.37; H, 4.23; N, 8.39%.

EXAMPLE 35

4-Hydroxy-6-(1-imidazolylmethyl)benzo[b]thiophene-2-carboxylic acid

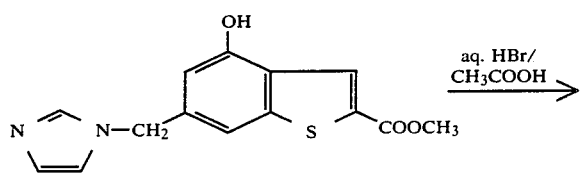

-continued

A mixture of 6-(1-imidazolylmethyl)-4-methoxybenzo[b]thiophene-2-carboxylic acid methyl ester (100 mg.), 48% aqueous hydrobromic acid (2.0 ml.) and acetic acid (1.0 ml.) was heated under reflux for 4 hours and then evaporated. The residue was dissolved in water and the solution was basified with sodium hydroxide solution and filtered. The filtrate was acidified with acetic acid and the solid was filtered off, washed with water and dried to give 4-hydroxy-6-(1-imidazolylmethyl)benzo[b]thiophene-2-carboxylic acid (52 mg.), m.p. 297°–299° C.

Analysis: Found: C, 56.42; H, 3.80; N, 9.84. $C_{13}H_{10}N_2O_3S$ Requires: C, 56.92; H, 3.67; N, 10.21%.

The following acids were prepared by the hydrolysis of the corresponding esters similarly to Example 33:

TABLE 5

| Example | Structure | m.p. °C. | Analysis |
|---|---|---|---|
| 36 | 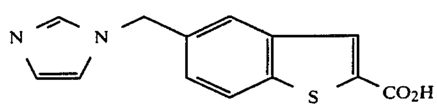 | 270–272[a] | Found: C, 60.06; H, 3.83; N, 10.68. $C_{13}H_{10}N_2O_2S$ Requires: C, 60.46; H, 3.90; N, 10.85%. |
| 37 | 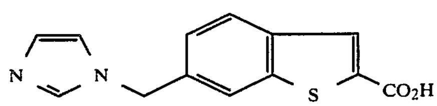 | 288–289[a] | Found: C, 60.32; H, 3.89; N, 10.84. $C_{13}H_{10}N_2O_2S$ Requires: C, 60.46; H, 3.90; N, 10.85%. |
| 38 | 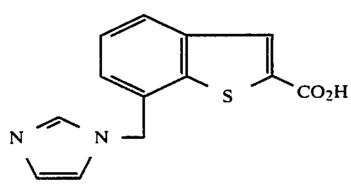 | 264–266[a] | Found: C, 60.17; H, 3.85; N, 10.92. $C_{13}H_{10}N_2O_2S$ Requires: C, 60.46; H, 3.90; N, 10.85%. |
| 39 | 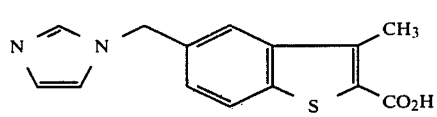 | 268–270 | Found: C, 61.54; H, 4.47; N, 10.11. $C_{14}H_{12}N_2O_2S$ Requires: C, 61.74; H, 4.44; N, 10.29%. |
| 40 | 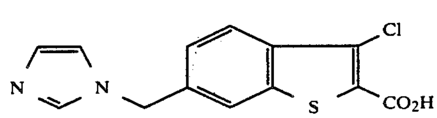 | 255–257 | Found: C, 53.58; H, 3.08; N, 9.62. $C_{13}H_9ClN_2O_2S$ Requires: C, 53.33; H, 3.10; N, 9.57%. |
| 41 | 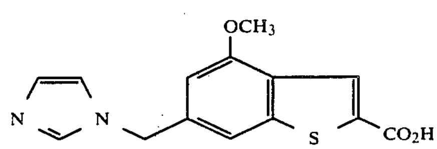 | 273–274 | Found: C, 58.55; H, 4.40; N, 9.85. $C_{14}H_{12}N_2O_3S$ Requires: C, 58.32; H, 4.20; N, 9.72%. |

TABLE 5-continued

| Example | Structure | m.p. °C. | Analysis |
|---|---|---|---|
| 42 | imidazol-1-ylmethyl at 5-position of benzo[b]thiophene-2-carboxylic acid | 235–237 | Found: C, 60.05; H, 3.95; N, 10.70. $C_{13}H_{10}N_2O_2S$ Requires: C, 60.45; H, 3.90; N, 10.85%. |
| 43 | imidazol-1-ylmethyl at 6-position of benzo[b]thiophene-2-carboxylic acid | 280–282 | Found: C, 60.13; H, 3.91; N, 10.89. $C_{13}H_{10}N_2O_2S$ Requires: C, 60.45; H, 3.90; N, 10.85%. |
| 44 | imidazol-1-ylmethyl at 7-position of benzo[b]thiophene-2-carboxylic acid | 276–277 | Found: C, 60.16; H, 4.04; N, 10.65. $C_{13}H_{10}N_2O_2S$ Requires: C, 60.45; H, 3.90; N, 10.85%. |
| 45 | 6-(imidazol-1-ylmethyl)-3-methylbenzo[b]thiophene-2-carboxylic acid | 265–267 | Found: C, 61.31; H, 4.47; N, 10.24. $C_{14}H_{12}N_2O_2S$ Requires: C, 61.74; H, 4.44; N, 10.29%. |
| 46 | 6-[2-(imidazol-1-yl)ethyl]-3-methylbenzo[b]thiophene-2-carboxylic acid | 233–236 | Found: C, 62.14; H, 5.02; N, 9.74. $C_{15}H_{14}N_2O_2S$ Requires: C, 62.91; H, 4.92; N, 9.78%. |
| 47 | 6-[2-(imidazol-1-yl)ethoxy]-3-methylbenzo[b]thiophene-2-carboxylic acid | 239–240 | Found: C, 59.28; H, 4.61; N, 8.99. $C_{15}H_{14}N_2O_3S$ Requires: C, 59.58; H, 4.67; N, 9.27%. |
| 48 | 5-[(pyridin-3-yloxy)methyl]benzo[b]thiophene-2-carboxylic acid | 215–216[b] | Found: C, 62.89; H, 3.92; N, 4.97. $C_{15}H_{11}NO_3S$ Requires: C, 63.14; H, 3.89; N, 4.91%. |
| 49 | 6-[(pyridin-3-yloxy)methyl]benzo[b]thiophene-2-carboxylic acid | 239–241[b] | Found: C, 63.15; H, 3.95; N, 4.90. $C_{15}H_{11}NO_3S$ Requires: C, 63.14; H, 3.89; N, 4.91%. |
| 50 | 7-[(pyridin-3-yloxy)methyl]benzo[b]thiophene-2-carboxylic acid | 246–249[c] | Found: C, 62.43; H, 3.89; N, 4.91. $C_{15}H_{11}NO_3S$ Requires: C, 63.14; H, 3.89; N, 4.91%. |
| 51 | 3-methyl-6-[(pyridin-3-yloxy)methyl]benzo[b]thiophene-2-carboxylic acid | 238–240 | Found: C, 64.38; H, 4.49; N, 4.98. $C_{16}H_{13}NO_3S$ Requires: C, 64.19; H, 4.38; N, 4.68%. |

TABLE 5-continued

| Example | Structure | m.p. °C | Analysis |
|---|---|---|---|
| 52 | 3-pyridyl-O-CH2- linked to benzothiophene with Cl at 3-position and CO2H at 2-position | 244–246 | Found: C, 56.84; H, 3.19; N, 4.68. $C_{15}H_{10}ClNO_3S$ Requires: C, 56.34; H, 3.15; N, 4.38%. |
| 53 | 3-pyridyl-O-CH2- linked to benzothiophene-2-CO2H | 238–240 | Found: C, 62.96; H, 3.80; N, 4.80. $C_{15}H_{11}NO_3S$ Requires: C, 63.14; H, 3.89; N, 4.91%. |
| 54 | 3-pyridyl-O-CH2- linked to 3-methylbenzothiophene-2-CO2H | 252–253 | Found: C, 64.01; H, 4.41; N, 4.76. $C_{16}H_{13}NO_3S$ Requires: C, 64.19; H, 4.38; N, 4.76%. |
| 55 | 3-pyridyl-O-CH2- linked to benzothiophene-3-CO2H | 216–217 | Found: C, 62.86; H, 4.12; N, 4.79. $C_{15}H_{11}NO_3S$ Requires: C, 63.14; H, 3.89; N, 4.91%. |
| 56* | 4-pyridyl-CH=CH- linked to 3-methylbenzothiophene-2-CO2K | >300 | Found: C, 59.8; H, 4.28; N, 4.21 $C_{17}H_{12}KNO_2S$ Requires: C, 61.23; H, 3.63; N, 4.20% |
| 57 | 4-pyridyl-CH2CH2- linked to 3-methylbenzothiophene-2-CO2H | >290 | Found: C, 68.53; H, 5.10; N, 4.68. $C_{17}H_{15}NO_2S$ Requires: C, 68.60; H, 5.08; N, 4.71%. |
| 58 | imidazol-1-yl-CH2- linked to benzofuran-2-CO2H | 273–275 | Found: C, 64.46; H, 4.09; N, 11.72. $C_{13}H_{10}N_2O_3$ Requires: C, 64.46; H, 4.16; N, 11.57%. |
| 59 | 3-pyridyl-CH2-O- linked to benzofuran-2-CO2H | 203–204 | Found: C, 66.59; H, 4.10; N, 5.30. $C_{15}H_{11}NO_4$ Requires: C, 66.91; H, 4.12; N, 5.20%. |
| 60 | imidazol-1-yl-CH2- linked to indole-2-CO2H | 275–277 | Found: C, 64.46; H, 4.52; N, 17.45. $C_{13}H_{11}N_3O_2$ Requires: C, 64.72; H, 4.60; N, 17.42%. |

TABLE 5-continued

| Example | Structure | m.p. °C. | Analysis |
|---|---|---|---|
| 61 | 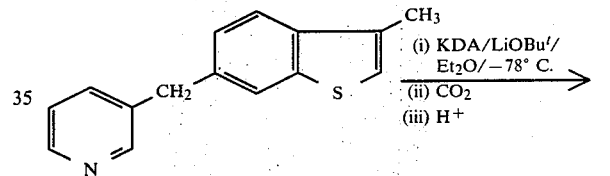 | 230–232 | Found: C, 71.82; H, 5.20; N, 12.36. $C_{20}H_{17}N_3O_2$ Requires: C, 72.49; H, 5.17; N, 12.68%. |

(a)Recrystallized from water.
(b)Crystallized from methanol/water.
(c)Crystallized from methanol.
*This compound was isolated as the potassium salt, the acidification step being omitted. The salt was hygroscopic.

EXAMPLE 62

3-Methyl-6-(3-pyridylmethyl)benzo[b]thiophene-2-carboxylic acid

(i) 6-(3-Methylbenzo[b]thienyl)-3-pyridyl ketone

A solution of 6-bromo-3-methylbenzo[b]thiophene (9.08 g.) and methyl iodide (2.52 g.) in dry ether (50 ml.) was added dropwise to magnesium (1.94 g.) covered by dry ether (50 ml.) at such a rate that the reaction was not too vigorous. The mixture was then heated under reflux for 2 hours and cooled. A solution of 3-cyanopyridine (8.33 g.) in dry ether (100 ml.) was added dropwise with vigorous stirring and the mixture was then stirred at 45° C. (bath temperature) for 2 hours. After cooling, 5N hydrochloric acid (200 ml.) was added cautiously to the mixture which was then shaken and filtered through "Hyflo" (Registered Trademark). The acidic layer was separated, heated on a steam bath for 30 minutes and then cooled and filtered through Hyflo to remove some tarry material. The filtrate was made just alkaline by the addition of 2N sodium hydroxide solution and then extracted several times with ethyl acetate. The combined extracts were washed well with water and dried ($Na_2SO_4$). Evaporation of the solvent gave an oil which was chromatographed on silica gel. Elution with chloroform gave first some impurity followed by product. Evaporation of the product-containing fractions gave a solid which was crystallized from methanol/water to give 6-(3-methylbenzo[b]thienyl)-3-pyridyl ketone (3.0 g.), m.p. 120°–121° C.

Analysis: Found: C, 70.85; H, 4.39; N, 5.33. $C_{15}H_{11}NOS$ Requires: C, 71.12; H, 4.38; N, 5.53%.

(ii) 3-Methyl-6-(3-pyridylmethyl)benzo[b]thiophene

A mixture of 6-(3-methylbenzo[b]thienyl)-3-pyridyl ketone (1.0 g.) 99% hydrazine hydrate (1.0 ml.) and diethylene glycol (5 ml.) was heated under reflux for 2 hours. The excess of water and hydrazine was distilled off until the temperature of the solution reached 190° C. The solution was then cooled to 90°–100° C. and potassium hydroxide (1.0 g.) was added. When the initial reaction had subsided the mixture was heated at 10° C. for 2 hours and then cooled and poured into water. The mixture was extracted several times with ether and the combined extracts were washed with water and dried ($Na_2SO_4$). Evaporation of the solvent gave an oil which was chromatographed on silica gel. Elution with chloroform gave, after elution of some impurity, pure 3-methyl-6-(3-pyridylmethyl)benzo[b]thiophene (0.80 g.) as an oil.

A portion was dissolved in ether and treated with an excess of ethereal hydrogen chloride. The solid was filtered off and crystallized from ethanol/ether to give 3-methyl-6-(3-pyridylmethyl)benzo[b]thiophenehydrochloride, m.p. 206°–207° C.

Analysis: Found: C, 65.02; H, 6.26; H, 5.02. $C_{15}H_{13}NSHCl$ Requires: C, 65.32; H, 5.12; N, 5.08%.

(iii) 3-Methyl-6-(3-pyridylmethyl)benzo[b]thiophene-2-carboxylic acid

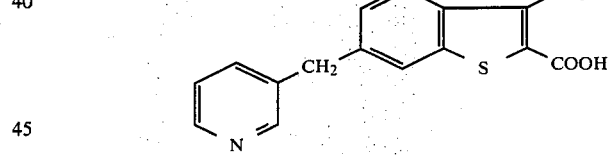

n-Butyl lithium (0.65 ml. of 1.55M solution in hexane) was added dropwise to a stirred mixture of diisopropylamine (0.10 g.) and potassium t-butoxide (0.11 g.) in dry ether (10 ml.) at −78° C. under an atmosphere of dry nitrogen. The mixture was stirred at −78° C. for 45 minutes and then a solution of 3-methyl-6-(3-pyridylmethyl)benzo[b]thiophene (0.20 g.) in dry ether (5 ml.) was added. The solution was stirred at −78° C. for 45 minues and then an excess of crushed solid carbon dioxide was added. When all the carbon dioxide had evaporated, water (5 ml.) was added and the mixture was shaken. The aqueous layer was then separated and washed with ether. It was then acidified with acetic acid and the solid was filtered off and dissolved in 2N sodium hydroxide. The solution was decolorized by warming with charcoal and then filtered. Acidification of the filtrate with acetic acid gave a solid which was filtered off, washed with water and dried to give 3-methyl-6-(3-pyridylmethyl)benzo[b]thiophene-2-carboxylic acid (0.10 g.), m.p. 250°–252° C.

Analysis: Found: 67.96; H, 4.59; N, 4.73. $C_{16}H_{13}NO_2S$ Requires: 67.82; H, 4.62; N, 4.94%.

EXAMPLE 63

6-[2-(1-Imidazolylethyl)]-3-methylbenzo[b]thiophene-2-carboxylic acid

(i) 2-Bromo-6-bromoacetyl-3-methylbenzo[b]thiophene

Bromine (1.67 g.) was added dropwise to a stirred solution of 6-acetyl-2-bromo-3-methylbenzo[b]-thiophene (2.50 g.) in a mixture of ether (15 ml.) and dioxan (15 ml.). The solution was stirred for 45 minutes and then diluted with water (100 ml.). The layers were separated and the aqueous layer was washed several times with ethyl acetate. The combined organic layer and extracts were washed with water and dried ($Na_2SO_4$). Evaporation of the solvent gave a solid which was chromatographed on silica gel. Elution with chloroform gave 2-bromo-6-bromoacetyl-3-methylbenzo[b]thiophene (2.75 g.) pure enough for further reaction. A sample crystallized from ethyl acetate/petrol (b.p. 60°–80°) had m.p. 126°–128° C.

Analysis: Found: C, 37.76; H, 2.36. $C_{11}H_8Br_2OS$ Requires: C, 37.95 H, 2.32%.

(ii) 2-Bromo-6-(1-imidazolyl)acetyl-3-methylbenzo[b]thiophene

A mixture of 2-bromo-6-bromoacetyl-3-methylbenzo[b]thiopene (1.74 g.), imidazole (0.34 g.) and sodium carbonate (1.50 g.) in acetone (20 ml.) was heated under reflux for 2 hours and then evaporated. Water (50 ml.) was added to the residue and the mixture was extracted several times with ethyl acetate. The combined extracts were dried ($Na_2SO_4$) and evaporated to give a solid which was chromatographed on silica gel. Elution with chloroform gave a solid which was crystallized from isopropanol/petrol (b.p. 60°–80°) to give 2-bromo-6-(1-imidazolyl)acetyl-3-methylbenzo[b]thiophene (0.55 g.), m.p. 184°–186° C.

Analysis: Found: C, 50.13; H, 3.33, N, 8.59. $C_{14}H_{11}BrN_2OS$ Requires: C, 50.16; H, 3.31; N, 8.36%.

(iii) 2-Bromo-6-[2-(1-imidazolyl)ethyl]-3-methylbenzo[b]thiophene

A mixture of 2-bromo-6-(1-imidazolyl)acetyl-3-methylbenzo[b]thiophene (0.45 g.), 99% hydrazine hydrate (0.20 g.) and ethylene glycol (5.0 ml.) was heated on a steam bath for 2 hours and then cooled. Potassium hydroxide (0.24 g.) was added and the mixture was heated at 135° C. for 1.5 hours and then cooled and poured into water. The mixture was extracted several times with ethyl acetate and the combined extracts were washed with water and dried ($Na_2SO_4$). Evaporation of the solvent gave an oil which as chromatographed on silica gel. Elution with chloroform gave a small amount of impurity followed by pure product. Evaporation of the product-containing fractions gave 2-bromo-6-[2-(1-imidazolyl)ethyl]-3-methylbenzo[b]thiophene (0.40 g.) as a thick oil which was pure enough for further reaction.

(iv) 6-[2-(1-Imidazolylethyl)]-3-methylbenzo[b]thiophene-2-carboxylic acid

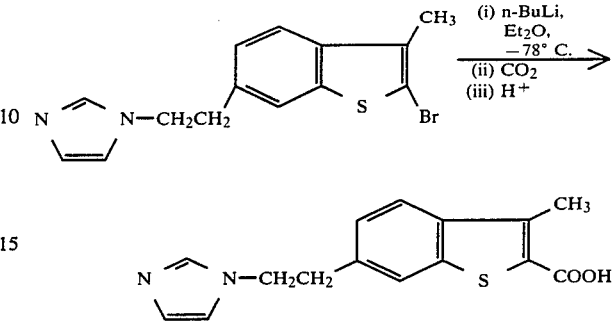

n-Butyl lithium (0.30 ml. of 1.55M solution in hexane) was added to a stirred mixture of 2-bromo-6-[2-(1-imidazolylethyl)]-3-methylbenzo[b]thiophene (0.15 g.) in dry ether (10 ml.) at −78° C. under an atmosphere of dry nitrogen. The mixture was stirred at −78° C. for 15 minutes and then an excess of crushed solid carbon dioxide was added. When all the carbon dioxide had evaporated water (5 ml.) was added and the mixture was shaken. The aqueous layer was separated, washed with ether and acidified with acetic acid. The solid was filtered off and dissolved in dilute sodium hydroxide solution. The solution was filtered and acidified with acetic acid. The solid was filtered off, washed with water and dried to give 6-[2-(1-imidazolylethyl]-3-methylbenzo[b]thiophene-2-carboxylic acid, m.p. 265°–267°.

Analysis: Found: 63.15; H, 4.85; N, 9.75. $C_{15}H_{14}N_2O_2S$ Requires: 62.90; H, 4.93; N, 9.78%.

EXAMPLE 64

3-Methyl-5-(3-pyridylmethyl)benzofuran-2-carboxylic acid

(i) 2-Acetyl-4-(3-pyridylmethyl)phenoxyacetic acid ethyl ester

Sodium hydride (0.96 g. of 50% dispersion in mineral oil) was added portionwise to a stirred solution of 2-hydroxy-5-(3-pyridylmethyl)acetophenone (4.54 g.) in dry N,N-dimethylformamide and the mixture was stirred for 1 hour at room temperature and then cooled to 0° C. Ethyl bromoacetate (3.34 g.) was then added dropwise with stirring and the mixture was stirred at room temperature for 3 hours and then poured into water. The mixture was extracted several times with ether and the combined extracts were washed well with water and dried ($Na_2SO_4$). Evaporation of the solvent gave crude 2-acetyl-4-(3-pyridylmethyl)phenoxyacetic acid ethyl ester (4.70 g.) which was used directly in the next stage.

(ii) 3-Methyl-5-(3-pyridylmethyl)benzofuran-2-carboxylic acid

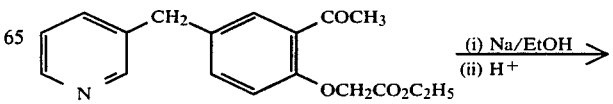

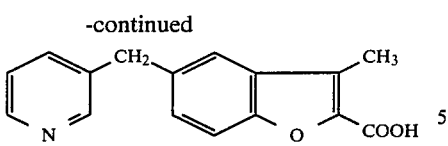

Sodium (0.50 g.) was dissolved in ethanol (10 ml.) and a solution of 2-acetyl-4-(3-pyridylmethyl)phenoxyacetic acid ethyl ester (4.70 g.) in ethanol (15 ml.) was added. The mixture was heated under reflux for 3 hours and then evaporated. The residue was dissolved in water and the solution was washed several times with ether. The aqueous layer was acidified with glacial acetic acid to give a gummy solid which was filtered off, washed with water, dried and chromatographed on silica gel. Elution with chloroform gave some impurity and then further elution with chloroform/methanl (9:1) gave a solid which was crystallized from ethanol to give 3-methyl-5-(3-pyridylmethyl)benzofuran-2-carboxylic acid (0.75 g.) m.p. 223-225° C.

Analysis: Found: C, 71.86; H, 4.98; N, 5.02. $C_{16}H_{13}NO_3$ Requires: C, 71.90; H, 4.90; N, 5.24%.

EXAMPLE 65
3-Methyl-5-(3-pyridylmethyl)benzofuran-2-carboxamide

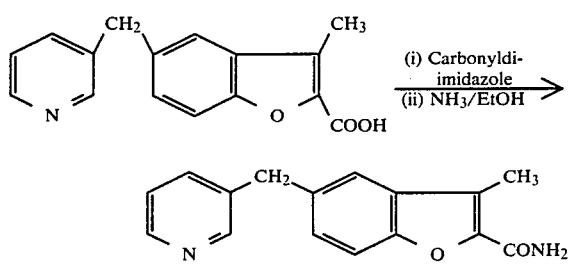

A mixture of 3-methyl-5-(3-pyridylmethyl)benzofura-2-carboxylic acid (0.28 g.), carbonyldiimidazole (0.28 g.) and dioxan (5 ml.) was heated on a steam bath for 2 hours and then evaporated. The residue was dissolved in a concentrated solution of ammonia in ethanol (10 ml.), the solution was allowed to stand for 30 minutes and then evaporated. The residue was chromatographed on silica gel. Elution with chloroform first gave a small amount of impurity followed by pure product. Evaporation of the product-containing fractions gave a solid which was crystallized from isopropanol/petrol (b.p 60°-80°) to give 3-methyl-5-(3-pyridylmethyl)benzofuran-2-carboxamide (0.16 g.), m.p. 175°-177° C.

Analysis: Found: C, 72.65; H, 5.43; N, 10.56. $C_{16}H_{14}N_2O_2$ Requires: C, 72.16; H, 5.30; N, 10.52%.

We claim:

1. A compound of the formula:

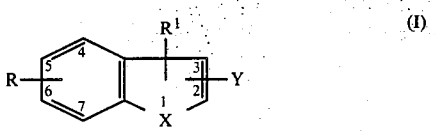

wherein
$R^1$, which is attached to the 2-, 3- or 4-position, is hydrogen, halogen, $C_1-C_4$ alkyl, hydroxy, or $C_1-C_4$ alkoxy;

Y, which is attached to the 2- or 3-position, is —COOH, —COO($C_1-C_4$ alkyl) or —CONH$_2$;
X is O, S, NH, N ($C_1-C_4$) alkyl or N(benzyl); and
R, which is attached to the 5-, 6- or 7-position, is (3- or 4-pyridyl)-$Z^2$— wherein
$Z^2$ is —CH$_2$—, —CH$_2$CH$_2$—, —CH=CH—, —CH$_2$O— or —OCH$_2$—; and the pharmaceutically acceptable salts thereof.

2. A compound according to claim 1:

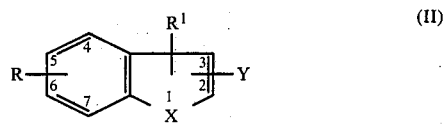

wherein $R^1$ is attached to the 2-or 3-position and is hydrogen, halogen, $C_1-C_4$ alkyl or $C_1-C_4$ alkoxy; and R is

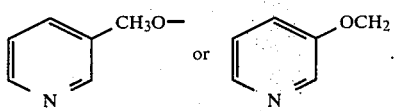

3. A compound according to claim 1 in which X is S; Y is —COOH, —COOCH$_3$, —COOC$_2$H$_5$ or —CONH$_2$; and $R^1$ is hydrogen, 3-chloro, 2- or 3-methyl, 4-methoxy or 4-hydroxy.

4. A compound according to claim 3 in which $R^1$ is hydrogen; R is (3-pyridyl)methoxy; and Y is —COOH or —COOCH$_3$.

5. A compound according to claim 4 wherein Y is —COOH; $R^1$ is hydrogen, 2- or 3-methyl, or 4-methoxy; and R is (3-pyridyloxy)methyl.

6. A compound of the formula:

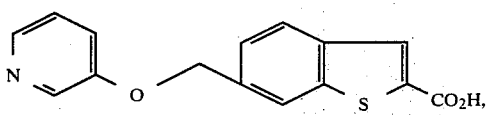

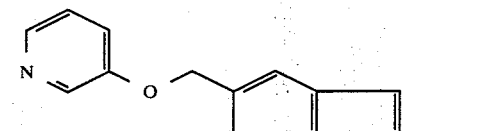

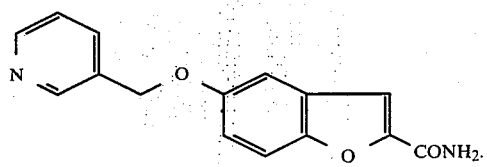

7. A compound according to claim 1 wherein X is O; R is (3-pyridyl)methyl, or (3-pyridyl)methoxy; $R^1$ is hydrogen or 3-methyl; and Y is —COOH, —COOCH$_3$ or —CONH$_2$.

8. A compound of the formula

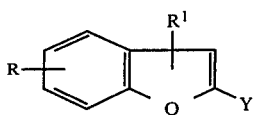

wherein R¹ which is attached to the 3- or 4-position is hydrogen or $C_1$-$C_4$ alkyl; Y is —COOH or —COO($C_1$-$C_4$ alkyl); R which is attached to the 5-, 6- or 7-position is (3- or 4-pyridyl)-$CH_2O$—; and the pharmaceutically acceptable salts thereof.

9. A pharmaceutical composition comprising a thromboxane synthetase enzyme inhibiting amount of a compound according to claim 1 together with a pharmaceutically acceptable diluent or carrier.

10. A method for treating a human being having a condition characterized by an imbalance of the prostacyclin:thromboxane $A_2$ ratio which comprises administering to said human a sufficient amount of a compound according to claim 1 to restore the prostacyclin:thromboxane $A_2$ balance in said human.

* * * * *